United States Patent
Aram et al.

(10) Patent No.: US 10,149,722 B2
(45) Date of Patent: *Dec. 11, 2018

(54) METHOD OF FABRICATING CUSTOMIZED PATIENT-SPECIFIC BONE CUTTING BLOCKS

(75) Inventors: Luke J. Aram, Warsaw, IN (US); William Bugbee, Warsaw, IN (US); Charles A. Engh, Jr., Warsaw, IN (US); Joseph Moskal, Warsaw, IN (US); Mark Pagnano, Warsaw, IN (US); Michael Swank, Warsaw, IN (US); Bryan Rose, Warsaw, IN (US); Jose F. Guzman, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1501 days.

This patent is subject to a terminal disclaimer.

(21) Appl. No.: 13/580,254

(22) PCT Filed: Feb. 23, 2011

(86) PCT No.: PCT/US2011/025905
§ 371 (c)(1),
(2), (4) Date: Aug. 21, 2012

(87) PCT Pub. No.: WO2011/106407
PCT Pub. Date: Sep. 1, 2011

(65) Prior Publication Data
US 2013/0066319 A1    Mar. 14, 2013

Related U.S. Application Data

(60) Provisional application No. 61/308,180, filed on Feb. 25, 2010.

(51) Int. Cl.
A61B 17/17    (2006.01)
A61B 34/10    (2016.01)

(52) U.S. Cl.
CPC ........ *A61B 34/10* (2016.02); *A61B 2034/102* (2016.02); *A61B 2034/105* (2016.02); *A61B 2034/108* (2016.02)

(58) Field of Classification Search
CPC .............................. A61B 17/56; G06F 19/321
(Continued)

(56) References Cited

U.S. PATENT DOCUMENTS 3,298,410 A    1/1967    Noboru
3,816,855 A    6/1974    Saleh
(Continued)

FOREIGN PATENT DOCUMENTS

DE    3339259 C1    3/1985
DE    3925488 A1    2/1990
(Continued)

OTHER PUBLICATIONS

Radermacher et al.; Image Guided Orthopedic Surgery Using Individual Templates; 10 pages.
(Continued)

*Primary Examiner* — Jan Christopher Merene
(74) *Attorney, Agent, or Firm* — Barnes & Thornburg LLP

(57) ABSTRACT

A number of orthopedic surgical instruments are also disclosed. A method, apparatus, and system for fabricating such instruments are also disclosed.

17 Claims, 16 Drawing Sheets

(58) Field of Classification Search
USPC ........... 606/279, 88, 86 R; 705/2, 3; 700/97;
128/898; 264/219, 222, 227
See application file for complete search history.

(56) References Cited

U.S. PATENT DOCUMENTS

| | | |
|---|---|---|
| 3,901,298 A | 8/1975 | Eby |
| 3,965,950 A | 6/1976 | MacDonald |
| 4,055,862 A | 11/1977 | Farling |
| 4,140,161 A | 2/1979 | Russo et al. |
| 4,197,886 A | 4/1980 | MacDonald |
| 4,436,684 A | 3/1984 | White |
| 4,719,907 A | 1/1988 | Banko et al. |
| 4,721,104 A | 1/1988 | Kaufman et al. |
| 4,759,350 A | 7/1988 | Dunn et al. |
| 4,787,383 A | 11/1988 | Kenna |
| 4,834,080 A | 5/1989 | Brown |
| 4,841,975 A | 6/1989 | Woolson |
| 4,860,735 A | 8/1989 | Davey et al. |
| 5,053,037 A | 10/1991 | Lackey |
| 5,067,964 A | 11/1991 | Richmond et al. |
| 5,122,144 A | 6/1992 | Bert et al. |
| 5,129,908 A | 7/1992 | Petersen |
| 5,186,174 A | 2/1993 | Schloendorff et al. |
| 5,258,032 A | 11/1993 | Bertin |
| 5,314,478 A | 5/1994 | Oka et al. |
| 5,314,482 A | 5/1994 | Goodfellow et al. |
| 5,360,446 A | 11/1994 | Kennedy |
| 5,370,692 A | 12/1994 | Fink et al. |
| 5,417,694 A | 5/1995 | Marik et al. |
| 5,423,828 A | 6/1995 | Benson |
| 5,445,642 A | 8/1995 | McNulty et al. |
| 5,448,489 A | 9/1995 | Reuben |
| 5,458,645 A | 10/1995 | Bertin |
| 5,462,549 A | 10/1995 | Glock |
| 5,474,559 A | 12/1995 | Bertin et al. |
| 5,510,066 A | 4/1996 | Fink et al. |
| 5,514,139 A | 5/1996 | Goldstein et al. |
| 5,518,680 A | 5/1996 | Cima et al. |
| 5,520,695 A | 5/1996 | Luckman |
| 5,542,947 A | 8/1996 | Treacy |
| 5,562,674 A | 10/1996 | Stalcup et al. |
| 5,601,563 A | 2/1997 | Burke et al. |
| 5,632,745 A | 5/1997 | Schwartz |
| 5,683,397 A | 11/1997 | Vendrely et al. |
| 5,683,466 A | 11/1997 | Vitale |
| 5,702,460 A | 12/1997 | Carls et al. |
| 5,722,978 A | 3/1998 | Jenkins, Jr. |
| 5,725,376 A | 3/1998 | Poirier |
| 5,733,292 A | 3/1998 | Gustilo et al. |
| 5,776,201 A | 7/1998 | Colleran et al. |
| 5,791,212 A | 8/1998 | Han |
| 5,869,170 A | 2/1999 | Cima et al. |
| 5,879,393 A | 3/1999 | Whiteside et al. |
| 5,885,296 A | 3/1999 | Masini |
| 5,885,298 A * | 3/1999 | Herrington et al. ............ 606/88 |
| 5,897,559 A | 4/1999 | Masini |
| 5,925,049 A | 7/1999 | Gustilo et al. |
| 5,942,370 A | 8/1999 | Neckers et al. |
| 5,980,526 A | 11/1999 | Johnson et al. |
| 5,989,261 A | 11/1999 | Walker et al. |
| 6,007,537 A | 12/1999 | Burkinshaw et al. |
| 6,024,746 A | 2/2000 | Katz |
| 6,080,196 A | 6/2000 | Bertin |
| 6,081,577 A | 6/2000 | Webber |
| 6,096,043 A | 8/2000 | Techiera et al. |
| 6,099,313 A | 8/2000 | Dorken et al. |
| 6,139,574 A | 10/2000 | Vacanti et al. |
| 6,161,080 A | 12/2000 | Aouni et al. |
| 6,176,874 B1 | 1/2001 | Vacanti et al. |
| 6,177,034 B1 | 1/2001 | Ferrone |
| 6,206,927 B1 | 3/2001 | Fell et al. |
| 6,220,122 B1 | 4/2001 | Forsell et al. |
| 6,241,735 B1 | 6/2001 | Marmulla |
| 6,244,141 B1 | 6/2001 | Han |
| 6,251,143 B1 | 6/2001 | Schwartz et al. |
| 6,319,006 B1 | 11/2001 | Scherer et al. |
| 6,322,728 B1 | 11/2001 | Brodkin et al. |
| 6,382,975 B1 | 5/2002 | Poirier |
| 6,383,221 B1 * | 5/2002 | Scarborough ....... A61F 2/30771 |
| | | 623/17.11 |
| 6,454,811 B1 | 9/2002 | Sherwood et al. |
| 6,463,351 B1 | 10/2002 | Clynch |
| 6,478,799 B1 | 11/2002 | Williamson |
| 6,510,334 B1 | 1/2003 | Schuster et al. |
| 6,530,958 B1 | 3/2003 | Cima et al. |
| 6,554,837 B1 | 4/2003 | Hauri et al. |
| 6,554,838 B2 | 4/2003 | McGovern et al. |
| 6,558,391 B2 | 5/2003 | Axelson et al. |
| 6,575,980 B1 | 6/2003 | Robie et al. |
| 6,626,945 B2 | 9/2003 | Simon et al. |
| 6,668,941 B2 | 12/2003 | Phillips et al. |
| 6,679,917 B2 | 1/2004 | Ek |
| 6,711,432 B1 | 3/2004 | Krause et al. |
| 6,712,824 B2 | 3/2004 | Millard et al. |
| 6,712,856 B1 | 3/2004 | Carignan et al. |
| 6,738,657 B1 | 5/2004 | Franklin et al. |
| 6,766,878 B2 | 7/2004 | Widmer et al. |
| 6,772,026 B2 | 8/2004 | Bradbury et al. |
| 6,814,735 B1 | 11/2004 | Zirngibl et al. |
| 6,916,324 B2 | 7/2005 | Sanford et al. |
| 6,932,842 B1 * | 8/2005 | Litschko ................. A61F 2/30 |
| | | 623/16.11 |
| 6,994,549 B2 | 2/2006 | Brodkin et al. |
| 7,033,361 B2 * | 4/2006 | Collazo ......................... 606/87 |
| 7,060,074 B2 | 6/2006 | Rosa et al. |
| 7,141,053 B2 | 11/2006 | Rosa et al. |
| 7,172,597 B2 | 2/2007 | Sanford |
| 7,175,435 B2 * | 2/2007 | Andersson et al. .......... 433/215 |
| 7,194,295 B2 | 3/2007 | Vilsmeier |
| 7,534,263 B2 | 5/2009 | Burdulis, Jr. et al. |
| 7,618,451 B2 | 11/2009 | Berez et al. |
| 7,632,279 B2 * | 12/2009 | Bastian ........................... 606/88 |
| 7,634,119 B2 * | 12/2009 | Tsougarakis et al. ........ 382/128 |
| 7,717,956 B2 | 5/2010 | Lang |
| 7,796,791 B2 | 9/2010 | Tsougarakis et al. |
| 7,824,181 B2 * | 11/2010 | Sers ................................ 433/76 |
| 7,981,158 B2 * | 7/2011 | Fitz et al. ................. 623/17.16 |
| 7,985,225 B2 * | 7/2011 | Johnson et al. ................. 606/79 |
| 7,988,691 B2 | 8/2011 | Schulze et al. |
| 8,265,949 B2 * | 9/2012 | Haddad ............................ 705/2 |
| 8,425,524 B2 * | 4/2013 | Aker et al. ...................... 606/88 |
| 8,457,930 B2 * | 6/2013 | Schroeder ........................ 703/1 |
| 8,460,303 B2 * | 6/2013 | Park ................................. 606/87 |
| 8,480,679 B2 * | 7/2013 | Park et al. ....................... 606/87 |
| 8,480,754 B2 * | 7/2013 | Bojarski et al. ............ 623/20.35 |
| 8,483,469 B2 * | 7/2013 | Pavlovskaia et al. ........ 382/131 |
| 8,532,361 B2 * | 9/2013 | Pavlovskaia et al. ........ 382/131 |
| 8,532,806 B1 * | 9/2013 | Masson ........................... 700/98 |
| D691,719 S * | 10/2013 | Park ............................ D24/140 |
| 8,560,047 B2 * | 10/2013 | Haider et al. ................. 600/407 |
| 8,591,516 B2 * | 11/2013 | Metzger et al. ................ 606/88 |
| 8,617,171 B2 * | 12/2013 | Park et al. ....................... 606/88 |
| 8,617,175 B2 * | 12/2013 | Park et al. ....................... 606/89 |
| 8,702,712 B2 * | 4/2014 | Jordan et al. ............... 606/86 R |
| 8,715,291 B2 * | 5/2014 | Park et al. ....................... 606/88 |
| 8,734,455 B2 * | 5/2014 | Park et al. ....................... 606/89 |
| 8,737,700 B2 * | 5/2014 | Park et al. ..................... 382/128 |
| 8,777,875 B2 * | 7/2014 | Park ............................... 600/587 |
| 8,784,495 B2 * | 7/2014 | Bonutti ...................... 623/20.14 |
| 8,794,977 B2 * | 8/2014 | McGuan et al. .............. 434/262 |
| 8,834,473 B2 * | 9/2014 | Dees et al. .................. 606/86 R |
| 8,834,490 B2 * | 9/2014 | Bonutti ........................... 606/130 |
| 8,968,321 B2 * | 3/2015 | Wright et al. ................... 606/88 |
| 8,974,459 B1 * | 3/2015 | Axelson et al. ............ 606/86 R |
| 9,786,022 B2 * | 10/2017 | Aram .................. A61B 17/155 |
| 2001/0016775 A1 * | 8/2001 | Scarborough ....... A61F 2/30771 |
| | | 623/17.16 |
| 2002/0029045 A1 | 3/2002 | Bonutti |
| 2002/0059049 A1 | 5/2002 | Bradbury et al. |
| 2002/0183760 A1 | 12/2002 | McGovern et al. |
| 2003/0055501 A1 | 3/2003 | Fell et al. |
| 2003/0225413 A1 | 12/2003 | Sanford et al. |
| 2004/0039259 A1 | 2/2004 | Krause et al. |

(56) References Cited

U.S. PATENT DOCUMENTS

| | | | |
|---|---|---|---|
| 2004/0092932 A1 | 5/2004 | Aubin et al. | |
| 2004/0117015 A1* | 6/2004 | Biscup | G16H 50/50 623/16.11 |
| 2004/0153087 A1 | 8/2004 | Sanford et al. | |
| 2004/0181144 A1 | 9/2004 | Cinquin et al. | |
| 2004/0185422 A1 | 9/2004 | Ulrich et al. | |
| 2004/0204760 A1 | 10/2004 | Fitz et al. | |
| 2004/0236424 A1 | 11/2004 | Berez et al. | |
| 2004/0249385 A1 | 12/2004 | Faoro | |
| 2004/0260301 A1* | 12/2004 | Lionberger et al. | 606/88 |
| 2005/0015003 A1 | 1/2005 | Lachner et al. | |
| 2005/0037320 A1 | 2/2005 | Poirier | |
| 2005/0043835 A1 | 2/2005 | Christensen | |
| 2005/0075641 A1 | 4/2005 | Singhatat et al. | |
| 2005/0133955 A1* | 6/2005 | Christensen | 264/219 |
| 2005/0170311 A1 | 8/2005 | Tardieu et al. | |
| 2005/0171545 A1 | 8/2005 | Walsh et al. | |
| 2005/0234461 A1* | 10/2005 | Burdulis et al. | 606/79 |
| 2005/0261697 A1 | 11/2005 | Canonaco et al. | |
| 2005/0267485 A1 | 12/2005 | Cordes et al. | |
| 2005/0267584 A1 | 12/2005 | Burdulis et al. | |
| 2006/0089621 A1 | 4/2006 | Fard | |
| 2006/0245627 A1 | 11/2006 | Nagamune | |
| 2007/0006887 A1 | 1/2007 | Milton | |
| 2007/0059665 A1* | 3/2007 | Orentlicher et al. | 433/173 |
| 2007/0198022 A1 | 8/2007 | Lang et al. | |
| 2007/0213738 A1 | 9/2007 | Martin et al. | |
| 2007/0226986 A1 | 10/2007 | Park et al. | |
| 2007/0233140 A1* | 10/2007 | Metzger et al. | 606/88 |
| 2007/0233141 A1 | 10/2007 | Park et al. | |
| 2007/0250169 A1 | 10/2007 | Lang | |
| 2007/0288030 A1 | 12/2007 | Metzger et al. | |
| 2008/0015602 A1* | 1/2008 | Axelson | 606/87 |
| 2008/0015607 A1 | 1/2008 | D'Alessio et al. | |
| 2008/0114370 A1* | 5/2008 | Schoenefeld | 606/96 |
| 2008/0147072 A1 | 6/2008 | Park et al. | |
| 2008/0183177 A1 | 7/2008 | Fox et al. | |
| 2008/0195107 A1 | 8/2008 | Cuckler et al. | |
| 2008/0228189 A1 | 9/2008 | Fox et al. | |
| 2008/0234685 A1 | 9/2008 | Gjerde | |
| 2008/0243127 A1 | 10/2008 | Lang et al. | |
| 2008/0257363 A1* | 10/2008 | Schoenefeld et al. | 128/897 |
| 2008/0262624 A1 | 10/2008 | White et al. | |
| 2008/0275452 A1* | 11/2008 | Lang et al. | 606/88 |
| 2008/0281328 A1 | 11/2008 | Lang et al. | |
| 2008/0281329 A1* | 11/2008 | Fitz et al. | 606/88 |
| 2008/0281426 A1* | 11/2008 | Fitz et al. | 623/17.16 |
| 2008/0287954 A1 | 11/2008 | Kunz et al. | |
| 2008/0306558 A1 | 12/2008 | Hakki | |
| 2008/0312659 A1* | 12/2008 | Metzger et al. | 606/87 |
| 2009/0018546 A1* | 1/2009 | Daley | 606/92 |
| 2009/0024131 A1* | 1/2009 | Metzger et al. | 606/88 |
| 2009/0087276 A1* | 4/2009 | Rose | 409/79 |
| 2009/0088674 A1 | 4/2009 | Caillouette et al. | 602/26 |
| 2009/0088753 A1* | 4/2009 | Aram et al. | 606/79 |
| 2009/0088754 A1* | 4/2009 | Aker et al. | 606/79 |
| 2009/0088755 A1* | 4/2009 | Aker et al. | 606/79 |
| 2009/0088758 A1* | 4/2009 | Bennett | 606/82 |
| 2009/0088759 A1* | 4/2009 | Aram et al. | 606/87 |
| 2009/0088760 A1* | 4/2009 | Aram et al. | 606/87 |
| 2009/0088761 A1* | 4/2009 | Roose et al. | 606/87 |
| 2009/0088763 A1* | 4/2009 | Aram et al. | 606/88 |
| 2009/0093816 A1 | 4/2009 | Roose et al. | |
| 2009/0099567 A1* | 4/2009 | Zajac | 606/79 |
| 2009/0131941 A1 | 5/2009 | Park et al. | |
| 2009/0131942 A1* | 5/2009 | Aker et al. | 606/88 |
| 2009/0138020 A1* | 5/2009 | Park et al. | 606/88 |
| 2009/0149977 A1* | 6/2009 | Schendel | 700/98 |
| 2009/0151736 A1* | 6/2009 | Belcher et al. | 128/898 |
| 2009/0157083 A1* | 6/2009 | Park et al. | 606/87 |
| 2009/0163922 A1* | 6/2009 | Meridew et al. | 606/88 |
| 2009/0164024 A1 | 6/2009 | Rudan et al. | |
| 2009/0222014 A1 | 9/2009 | Bojarski et al. | |
| 2009/0222016 A1 | 9/2009 | Park et al. | |
| 2009/0254093 A1* | 10/2009 | White et al. | 606/89 |
| 2009/0254367 A1* | 10/2009 | Belcher et al. | 705/2 |
| 2009/0270868 A1* | 10/2009 | Park et al. | 606/87 |
| 2009/0274350 A1 | 11/2009 | Pavlovskaia et al. | |
| 2009/0307893 A1* | 12/2009 | Burdulis et al. | 29/527.1 |
| 2010/0016947 A1 | 1/2010 | Dobak et al. | |
| 2010/0023015 A1 | 1/2010 | Park | |
| 2010/0087829 A1* | 4/2010 | Metzger et al. | 606/96 |
| 2010/0152782 A1* | 6/2010 | Stone et al. | 606/280 |
| 2010/0160917 A1 | 6/2010 | Fitz et al. | |
| 2010/0168754 A1 | 7/2010 | Fitz et al. | |
| 2010/0185202 A1* | 7/2010 | Lester et al. | 606/88 |
| 2010/0191244 A1* | 7/2010 | White et al. | 606/88 |
| 2010/0212138 A1* | 8/2010 | Carroll et al. | 29/446 |
| 2010/0217270 A1* | 8/2010 | Polinski et al. | 606/87 |
| 2010/0217338 A1* | 8/2010 | Carroll et al. | 606/86 R |
| 2010/0228257 A1 | 9/2010 | Bonutti | |
| 2010/0262150 A1 | 10/2010 | Lian | |
| 2010/0274253 A1 | 10/2010 | Ure | |
| 2010/0281678 A1* | 11/2010 | Burdulis et al. | 29/592 |
| 2010/0286700 A1 | 11/2010 | Snider et al. | |
| 2010/0303324 A1* | 12/2010 | Lang et al. | 382/131 |
| 2010/0305573 A1 | 12/2010 | Fitz et al. | |
| 2010/0324692 A1* | 12/2010 | Uthgenannt et al. | 623/20.35 |
| 2011/0015636 A1* | 1/2011 | Katrana et al. | 606/87 |
| 2011/0015639 A1 | 1/2011 | Metzger et al. | |
| 2011/0029091 A1* | 2/2011 | Bojarski et al. | 623/20.32 |
| 2011/0029116 A1* | 2/2011 | Jordan et al. | 700/98 |
| 2011/0054478 A1* | 3/2011 | Vanasse et al. | 606/87 |
| 2011/0066193 A1* | 3/2011 | Lang et al. | 606/86 R |
| 2011/0071533 A1* | 3/2011 | Metzger et al. | 606/88 |
| 2011/0092804 A1* | 4/2011 | Schoenefeld et al. | 600/416 |
| 2011/0093086 A1 | 4/2011 | Witt et al. | |
| 2011/0293581 A1* | 12/2011 | Lee et al. | 424/93.7 |
| 2012/0029520 A1 | 2/2012 | Lang et al. | |
| 2013/0006661 A1* | 1/2013 | Haddad | 705/2 |
| 2014/0163568 A1* | 6/2014 | Wong et al. | 606/96 |
| 2014/0200902 A1* | 7/2014 | Aram et al. | 705/2 |

FOREIGN PATENT DOCUMENTS

| | | |
|---|---|---|
| DE | 3902249 A1 | 8/1990 |
| DE | 4016704 C1 | 9/1991 |
| DE | 3717871 C3 | 5/1995 |
| EP | 97001 A1 | 12/1983 |
| EP | 337901 A1 | 10/1989 |
| EP | 0908836 A2 | 4/1999 |
| EP | 1013231 A2 | 6/2000 |
| EP | 1136041 A2 | 9/2001 |
| EP | 904158 B1 | 7/2002 |
| EP | 709061 B1 | 7/2003 |
| EP | 1348393 A1 | 10/2003 |
| EP | 1486900 A1 | 12/2004 |
| EP | 1498851 A1 | 1/2005 |
| EP | 1444957 B1 | 3/2007 |
| EP | 1938749 A2 | 7/2008 |
| EP | 1669033 B1 | 2/2009 |
| FR | 2819168 A1 | 7/2002 |
| GB | 2437003 A | 10/2007 |
| WO | 1989011257 A1 | 11/1989 |
| WO | 9325157 A1 | 12/1993 |
| WO | 1993025157 A1 | 12/1993 |
| WO | 9730641 A1 | 8/1997 |
| WO | 9800072 A1 | 1/1998 |
| WO | 1998032384 A1 | 7/1998 |
| WO | 1999032045 A1 | 7/1999 |
| WO | 2004000139 A1 | 12/2003 |
| WO | 2004032806 A1 | 4/2004 |
| WO | 2004017842 A2 | 6/2004 |
| WO | 2004049981 A2 | 6/2004 |
| WO | 2004075771 A1 | 9/2004 |
| WO | 2005018453 A1 | 3/2005 |
| WO | 2005051239 A1 | 6/2005 |
| WO | 2005051240 A1 | 6/2005 |
| WO | 2005053564 A2 | 6/2005 |
| WO | 2006058057 A2 | 6/2006 |
| WO | 2006060795 A1 | 6/2006 |
| WO | 2007092841 A2 | 8/2007 |
| WO | 2007097853 A2 | 8/2007 |
| WO | 2007097854 A2 | 8/2007 |

(56) References Cited

FOREIGN PATENT DOCUMENTS

| WO | 2007145937 A2 | 12/2007 |
| WO | 2008021494 A2 | 2/2008 |
| WO | 2008112996 A1 | 9/2008 |
| WO | 2008117028 A1 | 10/2008 |
| WO | 2009001083 A1 | 12/2008 |
| WO | 2009045960 A1 | 4/2009 |
| WO | 2009111512 A2 | 9/2009 |
| WO | 2009129063 A1 | 10/2009 |
| WO | 2009129067 A1 | 10/2009 |
| WO | 2010033431 A1 | 3/2010 |

OTHER PUBLICATIONS

Radermacher et al.; Computer Assisted Matching of Planning and Execution in Orthopedic Surgery; 1993; 2 pages.

Radermacher et al.; Technique for Better Execution of CT Scan Planned Orthopedic Surgery on Bone Structures; 9 pages.

Radermacher et al.; Computer Assisted Orthopaedic Surgery with Image Based Individual Templates; No. 354, pp. 28-38; 1998; 11 pages.

Sharma et al.; The Role of Knee Alignment in Disease Progression and Functional Decline in Knee Osteoarthritis; Jul. 11, 2001; American Medical Association; 10 pages.

Berry, Seedhom, et al., "Personalised image-based templates for intra-operative guidance," Proceedings of the Institution of Mechanical Engineers, Part H: Journal of Engineering in Medicine, 111-118, 2005.

SurgiTAIX AG, "OrthoTAIX for Orthopaedic Surgery." Available at http://www.surgitaix.com/Products/OrthoTAIX/OrthoTAIX.pdf.

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P. Nolte and R. Ganz, eds, 42-52, Hogrefe & Huber Publishing 1999.

Portheine et al.; Development of a clinical demonstrator fro computer assisted orthopedic surgery with CT-image based individual templates; 1997; 6 pages.

PCT International Search Report for International Application No. PCT/US2011/025907, dated Apr. 12, 2011.

European Search Report; European Patent Application No. 08165418. 8-2165; dated Jan. 23, 2009; 6 pages.

Hube et al.; Orthopaedic Surgery the Essentials, Chaper 36 Knee Reconstruction; 1999; 12 pages.

Corin Medical Limited; The Corin X-ActTM Instrumentation and Operative Technique; Nov. 1998; 9 pages.

Kraus et al.; A Comparative Assessment of Alignment Angle of the Knee by Radiographic and Physical Examination Methods; Jun. 6, 2005; 6 pages.

Depuy; LCS Total Knee System—Surgical Procedure; 1989; 36 pages.

Engh et al.; Legent II Surgical Technique; The Concept of Personalization—Total Knee Replacement Using the AMK—Legend II; 1992; 31 pages.

Lotke; Knee Arthroplasty; Primary Total Knees—Standard Principles and Techniques; Raven Press, Ltd.; 5 pages; 1995.

Mills et al.; Use of Computer Tomographic Reconstruction in Planning Osteotomies of the Hip; Jan. 1992; 6 pages.

\* cited by examiner

METHOD OF FABRICATING CUSTOMIZED PATIENT-SPECIFIC BONE CUTTING BLOCKS

This application is a national stage entry under 35 USC § 371(b) of International Application No. PCT/US2011/025905, filed Feb. 23, 2011, which claims priority under 35 U.S.C. § 119(e) to U.S. Provisional Patent Application Ser. No. 61/308,180, entitled "Method of Fabricating Customized Patient-Specific Bone Cutting Blocks," which was filed on Feb. 25, 2010 by Jose Guzman et al., the entirety of both of which are incorporated herein by reference.

CROSS-REFERENCE TO RELATED U.S. PATENT APPLICATIONS

Cross-reference is made to co-pending U.S. Utility patent application Ser. Nos. 12/240,985; 12/240,990; 12/240,988; 12/240,992; 12/240,994; 12/240,996; 12/240,997; 12/240,998; 12/241,006; 12/241,002; 12/241,001; and 12/240,999. Each of these applications was filed on Sep. 29, 2008, and is assigned to the same assignee as the present application. Each of these applications is hereby incorporated by reference.

TECHNICAL FIELD

The present disclosure relates generally to customized patient-specific orthopaedic surgical instruments and to methods, devices, and systems for fabricating and positioning such instruments.

BACKGROUND

Joint arthroplasty is a well-known surgical procedure by which a diseased and/or damaged natural joint is replaced by a prosthetic joint. A typical knee prosthesis includes a tibial tray, a femoral component, a polymer insert or bearing positioned between the tibial tray and the femoral component, and, in some cases, a polymer patella button. To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

SUMMARY

According to one aspect, a method for a vendor to create a customized patient-specific orthopaedic instrument for a patient of a healthcare facility that is external to the vendor includes receiving, from the healthcare facility external to the vendor, an instrument request that includes data relevant to a bone of the patient. In response to receiving the instrument request, a surgical design plan is created that is customized for the patient per data of the instrument request. The surgical design plan includes a preoperatively planned size of at least one bone chip produced as a result of a surgical resection of the bone of the patient consistent with the surgical design plan. The surgical design plan is then sent to the healthcare facility.

A manufacturing machine located at the vendor may be operated to fabricate the customized patient-specific orthopaedic instrument per data of the surgical design plan, with the fabricated customized patient-specific orthopaedic instrument then being sent to the healthcare facility.

The surgical design plan may be transmitted to the healthcare facility via a network. In some embodiments, the surgical design plan is mailed to the healthcare facility.

The data relevant to the bone of the patient may include one or more medical images of the bone of the patient, and the surgical design plan may be created based upon the one or more medical images of the bone of the patient.

The data relevant to the bone of the patient may include one or more medical images of the femur of the patient. The surgical design plan may include a preoperatively planned size of a distal medial bone chip produced as a result of a surgical resection of the distal medial portion of the patient's distal femur consistent with the surgical design plan. The surgical design plan may also include a preoperatively planned size of a distal lateral bone chip produced as a result of a surgical resection of the distal lateral portion of the patient's distal femur consistent with the surgical design plan.

The surgical design plan may also include a preoperatively planned size of a posterior medial bone chip produced as a result of a surgical resection of the posterior medial portion of the patient's distal femur consistent with the surgical design plan, and a posterior lateral bone chip produced as a result of a surgical resection of the posterior lateral portion of the patient's distal femur consistent with the surgical design plan.

The data relevant to the bone of the patient may include one or more medical images of the tibia of the patient. The surgical design plan may include a preoperatively planned size of a bone chip produced as a result of a surgical resection of the proximal medial portion and the proximal lateral portion of the patient's proximal tibia consistent with the surgical design plan.

The surgical design plan may include a visual indication of the bone chip produced as a result of the surgical resection of the bone of the patient consistent with the surgical design plan.

According to another aspect, a method of performing an orthopaedic surgical procedure on a bone of a patient at a healthcare facility includes making a cut in the bone of the patient at a location indicated in a surgical design plan obtained from a vendor that is external to the healthcare facility that has been customized for the patient per data relevant to a bone of the patient. The surgical design plan may include a preoperatively planned size of a bone chip produced as a result of the cut. The actual size of the bone chip produced as a result of the cut may then be measured, with the measured actual size of the bone chip then being compared to the preoperatively planned size of the bone chip of the surgical design plan.

The cut may be made with a customized patient-specific orthopaedic cutting block fabricated per data of the surgical design plan.

The cut in the bone of the patient may be made at a location indicated in a surgical design plan obtained from a vendor that is external to the healthcare facility that has been customized for the patient per one or more medical images of the bone of the patient.

The surgical design plan may include a preoperatively planned size of a distal medial bone chip produced as a result of a surgical resection of the distal medial portion of the patient's distal femur consistent with the surgical design plan. The surgical design plan may also include a preoperatively planned size of a distal lateral bone chip produced as a result of a surgical resection of the distal lateral portion of the patient's distal femur consistent with the surgical design plan.

The surgical design plan may also include a preoperatively planned size of a posterior medial bone chip produced as a result of a surgical resection of the posterior medial portion of the patient's distal femur consistent with the surgical design plan, and a posterior lateral bone chip produced as a result of a surgical resection of the posterior lateral portion of the patient's distal femur consistent with the surgical design plan.

The surgical design plan may include a preoperatively planned size of a bone chip produced as a result of a surgical resection of the proximal medial portion and the proximal lateral portion of the patient's proximal tibia consistent with the surgical design plan.

The actual size of the bone chip may be measured with calipers.

According to another aspect, a method of performing an orthopaedic surgical procedure on a bone of a patient includes preoperatively planning a size of a bone chip to be produced by resecting the bone of the patient at a predetermined location. A cut is made in the bone of the patient at the predetermined location thereby producing a bone chip. The actual size of the bone chip produced as a result of the cut is measured and compared to the preoperatively planned size of the bone chip.

The bone of the patient is re-cut if the measured actual size of the bone chip is smaller than the preoperatively planned size of the bone chip.

The actual size of the bone chip may be measured with calipers.

BRIEF DESCRIPTION OF THE DRAWINGS

The detailed description particularly refers to the following figures, in which.

DETAILED DESCRIPTION OF THE DRAWINGS

Figure 1:
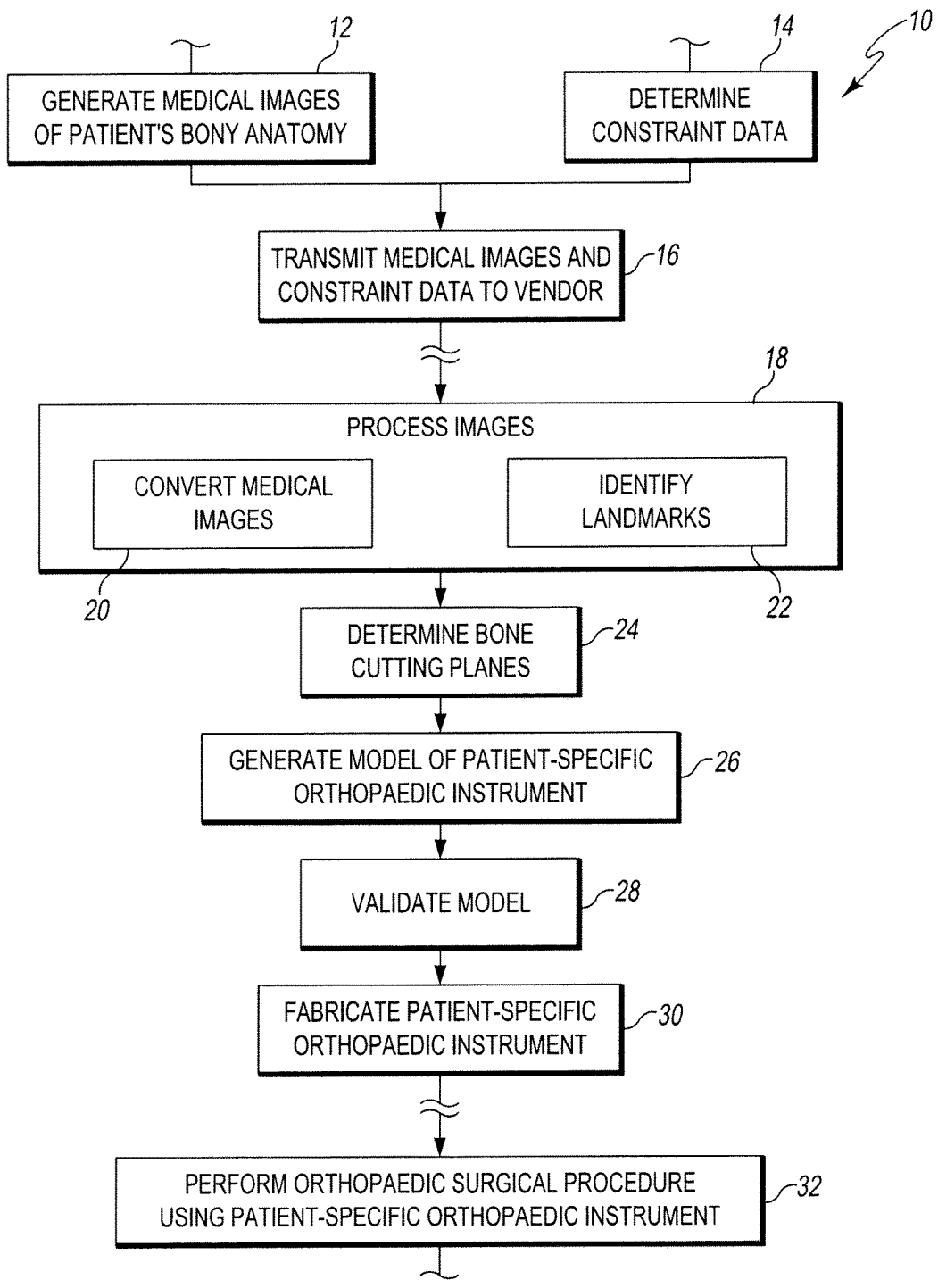
FIG. 1 is a simplified flow diagram of an algorithm for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to the orthopaedic implants and instruments described herein, along with a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

In some embodiments, the customized patient-specific orthopaedic surgical instrument may be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intra-operative decision-making with respect to the placement of the orthopaedic surgical instrument are reduced. For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument on the bone or bones of the patient in the unique location. When so coupled, the cutting plane, drilling holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling guide, a milling guide, or other type of orthopaedic surgical instrument configured to be coupled to a bone of a patient.

As shown in FIG. 1, the algorithm 10 includes process steps 12 and 14, in which an orthopaedic surgeon performs pre-operative planning of the orthopaedic surgical procedure to be performed on a patient. The process steps 12 and 14 may be performed in any order or contemporaneously with each other. In process step 12, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as any number of computed tomography (CT) images, magnetic resonance imaging (MRI) images, or other three-dimensional medical images. Additionally or alternatively, as discussed in more detail below in regard to process step 18, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's knee joint.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for a metal-on-metal interface, amount of inclination for implantation, the thickness of the bone to resect, size range of the orthopaedic implant, and/or the like. In some embodiments, the orthopaedic surgeon's preferences are saved as a surgeon's profile, which may used as a default constraint values for further surgical plans.

In process step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer process the medical images to facilitate the determination of the bone cutting planes, implant sizing, and fabrication of the customized patient-specific orthopaedic surgical instrument as discussed in more detail below. For example, in process step 20 the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application. Further, in some embodiments, an algorithm may be used to account for tissue such as cartilage not discernable in the generated medical images. In such embodiments, any three-dimensional model of the patient-specific instrument (see, e.g., process step 26 below) may be modified according to such algorithm to increase the fit and function of the instrument.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the cutting planes of the patient's bone are determined. The planned cutting planes are determined based on the type, size, and position of the orthopaedic prosthesis to be used during the orthopaedic surgical procedure, on the process images such as specific landmarks identified in the images, and on the constraint data supplied by the orthopaedic surgeon in process steps 14 and 16. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bony anatomy of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the selected orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's rotation with respect to bony landmarks such as the femoral epicondyle, posterior condyles, sulcus groove (Whiteside's line), and the mechanical axis as defined by the hip, knee, and/or ankle centers.

The planned cutting planes for the patient's bone(s) may then be determined based on the determined size, location, and orientation of the orthopaedic prosthesis. In addition, other aspects of the patient's bony anatomy, as determined in process step 22, may be used to determine or adjust the planned cutting planes. For example, the determined mechanical axis, landmarks, and/or other determined aspects of the relevant bones of the patient may be used to determine the planned cutting planes.

Along with determining the planned cutting planes, the planned sizes of the resultant bone chips are also determined. In particular, the preoperative surgical design plan created by the vendor includes a determination of the size of the bone chips that will be created when a surgeon executes the surgical design plan and resects the patient's bone along the planned cutting planes. In other words, a part of the surgical design plan is to create a model that includes the individual sizes of the "bone scrap" created by proper execution of the surgical design plan. As will be discussed below in greater detail, inclusion of the size of the bone chips created by proper execution of the surgical design plan provides a relatively easy way for the surgeon to confirm conformance with the surgical design plan. For example, if the surgical design plan preoperatively informs the surgeon that a proper resection of the distal lateral portion of the patient's femur along the planned cutting plane results in a distal lateral bone chip that is 11.0 mm thick, the surgeon can quickly and easily confirm his conformance with the surgical design plan by simply measuring the thickness of the distal lateral bone chip with, for example, a set of calipers after it has been resected from the patient's femur.

In the case of creation of a customized patient-specific femoral cutting block, the surgical design plan may include a model of the planned size of a distal medial bone chip produced as a result of a surgical resection of the distal medial portion of the patient's distal femur (DMF) consistent with the surgical design plan. It may also include the planned size of a distal lateral bone chip produced as a result of a surgical resection of the distal lateral portion of the patient's distal femur (DLF) consistent with the surgical design plan. The surgical design plan for use with a customized patient-specific femoral cutting block may also include the size of a posterior medial bone chip produced as a result of a surgical resection of the posterior medial portion of the patient's distal femur (PMF) consistent with the surgical design plan, and a posterior lateral bone chip produced as a result of a surgical resection of the posterior lateral portion of the patient's distal femur (PLF) consistent with the surgical design plan.

In the case of creation of a customized patient-specific tibial cutting block, the surgical design plan may include a model of the planned size of the bone chip (or chips) produced as a result of a surgical resection of the proximal medial portion (MT) and the proximal lateral portion (LT) of the patient's proximal tibia consistent with the surgical design plan.

In process step 26, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the customized patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling guide, a milling guide, and/or any other type of orthopaedic surgical tool or instrument.

The particular shape of the customized patient-specific orthopaedic surgical instrument is determined based on the planned location of the orthopaedic surgical instrument relative to the patient's bony anatomy. The location of the customized patient-specific orthopaedic surgical instrument with respect to the patient's bony anatomy is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 24. For example, in embodiments wherein the customized patient-specific orthopaedic surgical instrument is embodied as a bone-cutting block, the location of the orthopaedic surgical instrument is selected such that the cutting guide of the bone-cutting block matches one or more of the planned cutting planes determined in process step 24. Additionally, the planned location of the orthopaedic surgical instrument may be based on the identified landmarks of the patient's bone identified in process step 22.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to one or more of the bone cutting plane(s) as discussed above.

One illustrative embodiment of a method 40 for generating a model, such as a computer model, of a patient-specific orthopaedic instrument is illustrated in FIGS. 2 through 9. The method 40 begins with a step 42 in which a cartilage thickness value is determined. The cartilage thickness value is indicative of the average thickness of the cartilage of the patient's bone. As such, in one embodiment, the cartilage thickness value is equal to the average thickness of cartilage for an individual having similar characteristics as the patient. For example, the cartilage thickness value may be equal to the average thickness value of individuals of the same gender as the patient, the same age as the patient, having the same activity level of the patient, and/or the like. In other embodiments, the cartilage thickness value is determined based on one or more medical images of the patient's bone, such as those images transmitted in process step 16.

In step 44, a reference contour of the patient's relevant bone is determined. The reference contour is based on the surface contour of a three-dimensional model of the patient's relevant bone, such as the three-dimensional model generated in step 20. Initially the reference contour is identical to a region (i.e. the region of interest such as the distal end of the patient's femur or the proximal end of the patient's tibia) of the patient's bone. That is, in some embodiments, the reference contour is juxtaposed on the surface contour of the region of the patient's bone.

Subsequently, in step 46, the reference contour is scaled to compensate for the cartilage thickness value determined in step 42. To do so, in one embodiment, the scale of the reference contour is increased based on the cartilage thickness value. For example, the scale of the reference contour may be increased by an amount equal to or determined from the cartilage thickness value. However, in other embodiments, the reference contour may be scaled using other techniques designed to scale the reference contour to a size at which the reference contour is compensated for the thickness of the cartilage on the patient's bone.

Figure 3:
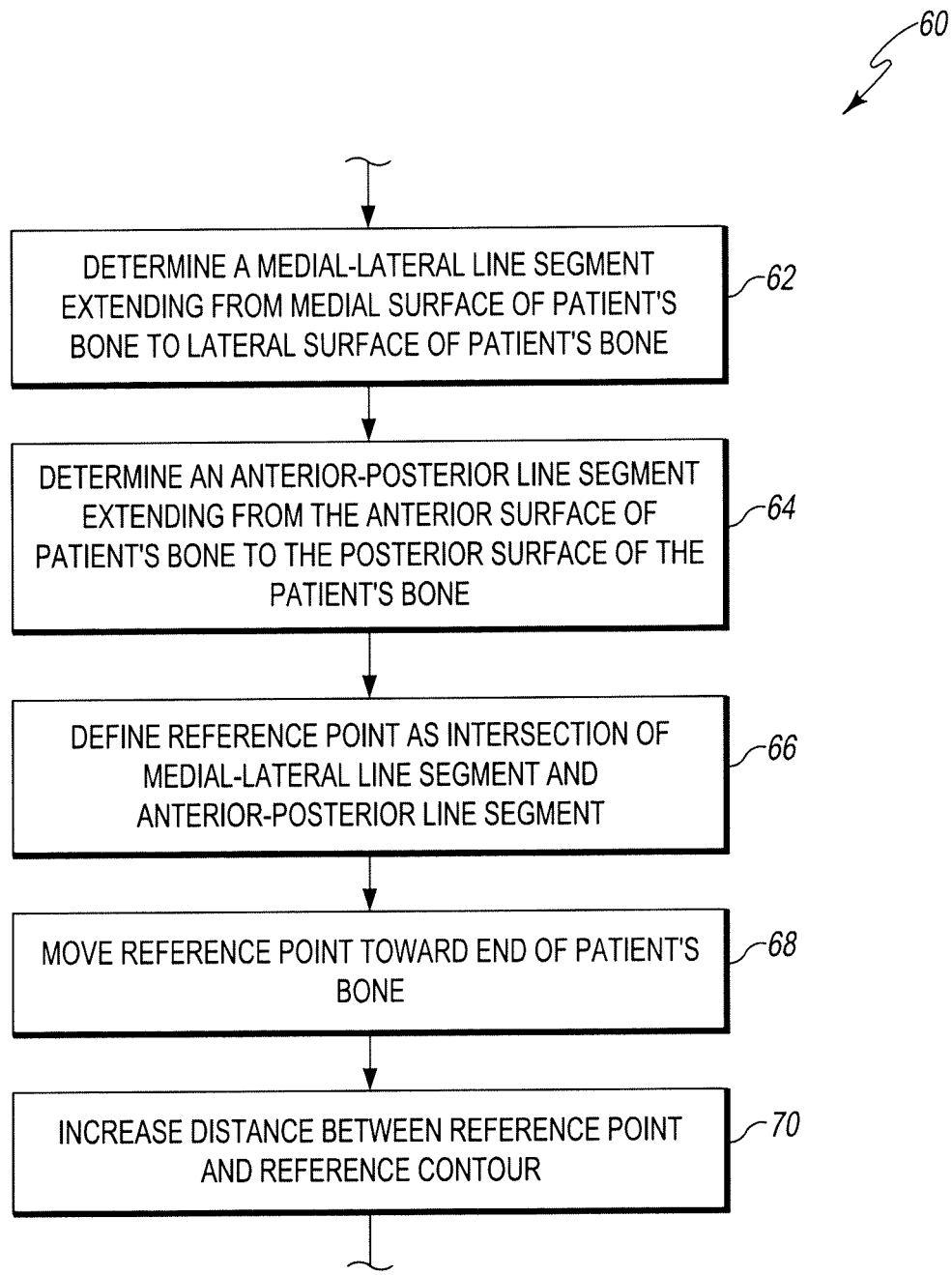
FIG. 3 is a simplified flow diagram of a method for scaling a reference contour.

For example, in one particular embodiment, the reference contour is scaled by increasing the distance between a fixed reference point and a point lying on, and defining in part, the reference contour. To do so, in one embodiment, a method 60 for scaling a reference contour as illustrated in FIG. 3 may be used. The method 60 begins with step 62 in which a medial/lateral line segment is established on the three-dimensional model of the patient's relevant bone. The medial/lateral line segment is defined or otherwise selected so as to extend from a point lying on the medial surface of the patient's bone to a point lying on lateral surface of the patient's bone. The medial surface point and the lateral surface point may be selected so as to define the substantially maximum local medial/lateral width of the patient's bone in some embodiments.

In step 64, an anterior/posterior line segment is established on the three-dimensional model of the patient's relevant bone. The anterior/posterior line segment is defined or otherwise selected so as to extend from a point lying on the anterior surface of the patient's bone to a point lying on posterior surface of the patient's bone. The anterior surface point and the posterior surface point may be selected so as to define the substantially maximum local anterior/posterior width of the patient's bone in some embodiments.

The reference point from which the reference contour will be scaled is defined in step 66 as the intersection point of the medial/lateral line segment and anterior/posterior line segment. As such, it should be appreciated that the medial surface point, the lateral surface point, the anterior surface point, and the posterior surface point lie on the same plane. After the reference point is initially established in step 66, the reference point is moved or otherwise translated toward an end of the patient's bone. For example, in embodiments wherein the patient's bone is embodied as a femur, the reference point is moved inferiorly toward the distal end of the patient's femur. Conversely, in embodiments when the patient's bone is embodied as a tibia, the reference point is moved superiorly toward the proximal end of the patient's tibia. In one embodiment, the reference point is moved a distance equal to about half the length of the anterior/posterior line segment as determined in step 64. However, in other embodiments, the reference point may be moved other distances sufficient to compensate the reference contour for thickness of the cartilage present on the patient's bone.

Once the location of the reference point has been determined in step 68, the distance between the reference point and each point lying on, and defining in part, the reference contour is increased in step 70. To do so, in one particular embodiment, each point of the reference contour is moved a distance away from the reference point based on a percentage value of the original distance defined between the reference point and the particular point on the reference contour. For example, in one embodiment, each point lying on, and defining in part, the reference contour is moved away from the reference point in by a distance equal to a percentage value of the original distance between the reference point and the particular point. In one embodiment, the percentage value is in the range of about 5 percent to about thirty percent. In one particular embodiment, the percentage value is about ten percent.

Figure 4:
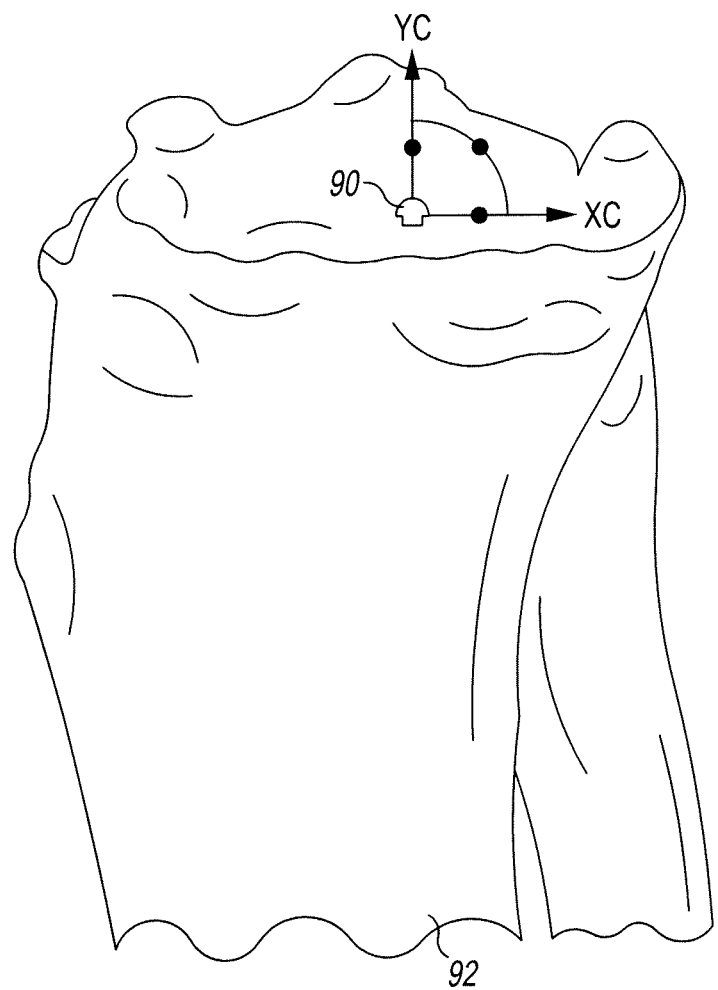
FIGS. 4-6 are three-dimensional model's of a patient's tibia.
Figure 5:
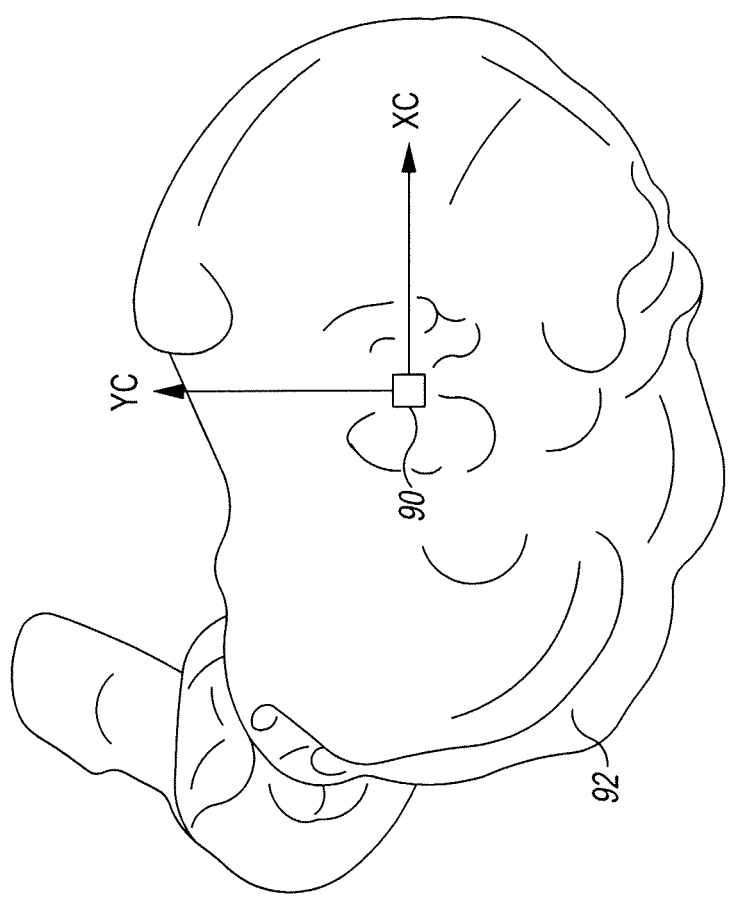
Figure 6:
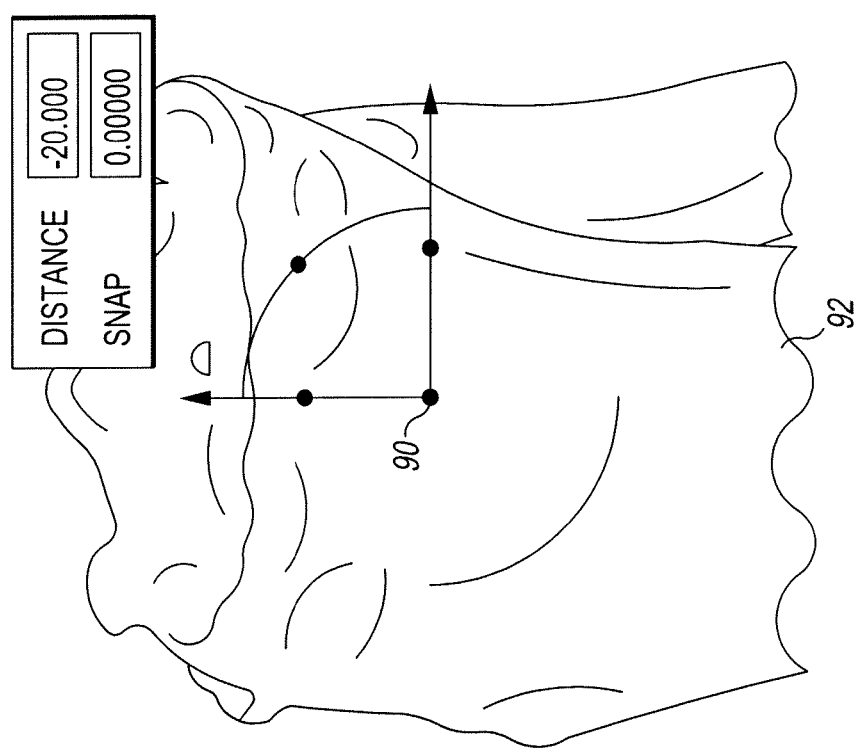

Referring now to FIGS. 4-9, in another embodiment, the reference contour is scaled by manually selecting a local "high" point on the surface contour of the three-dimensional image of the patient's bone. For example, in embodiments wherein the relevant patient's bone is embodied as a tibia as illustrated in FIGS. 4-6, the reference point 90 is initially located on the tibial plateau high point of the tibial model 92. Either side of the tibial plateau may be used. Once the reference point 90 is initially established on the tibial plateau high point, the reference point 90 is translated to the approximate center of the plateau as illustrated in FIG. 5 such that the Z-axis defining the reference point is parallel to the mechanical axis of the tibial model 92. Subsequently, as illustrated in FIG. 6, the reference point is moved in the distal direction by a predetermined amount. In one particular embodiment, the reference point is moved is the distal direction by about 20 millimeters, but other distances may be used in other embodiments. For example, the distance over which the reference point is moved may be based on the cartilage thickness value in some embodiments.

Figure 7:
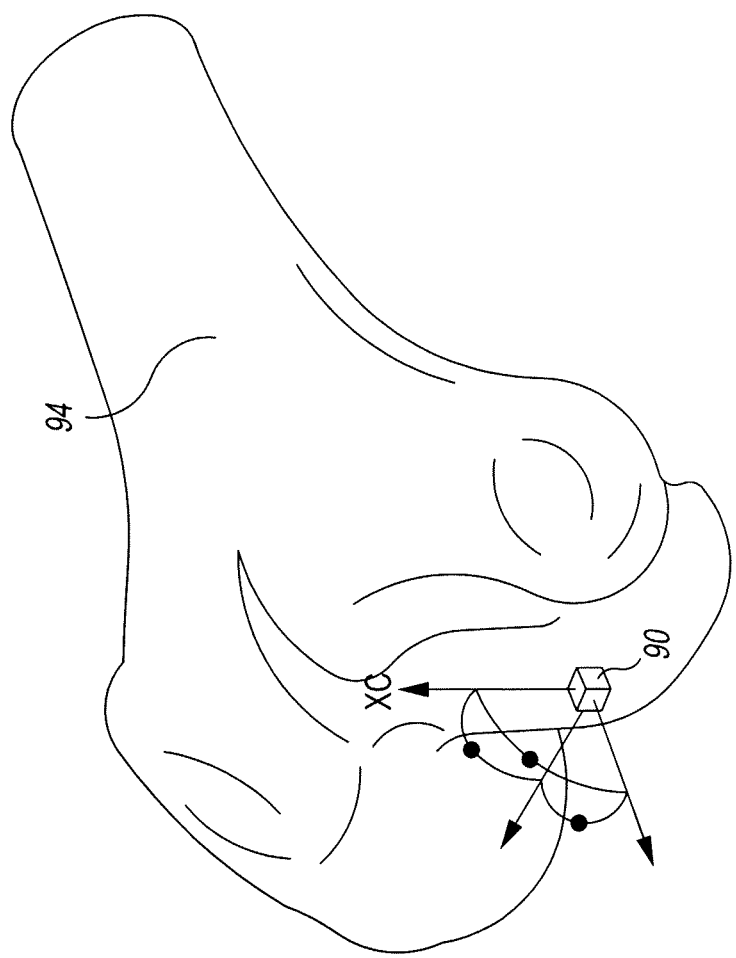
FIG. 7-9 are three-dimensional models of a patient's femur.
Figure 8:
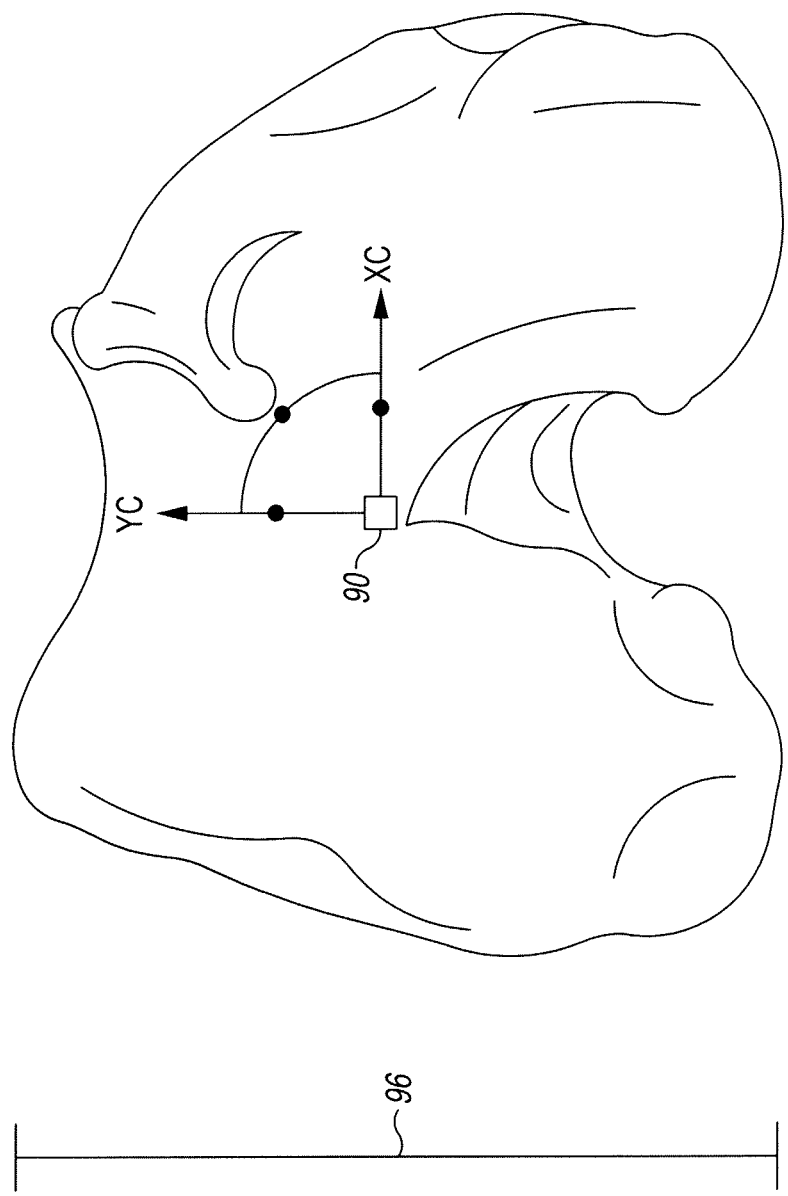
Figure 9:
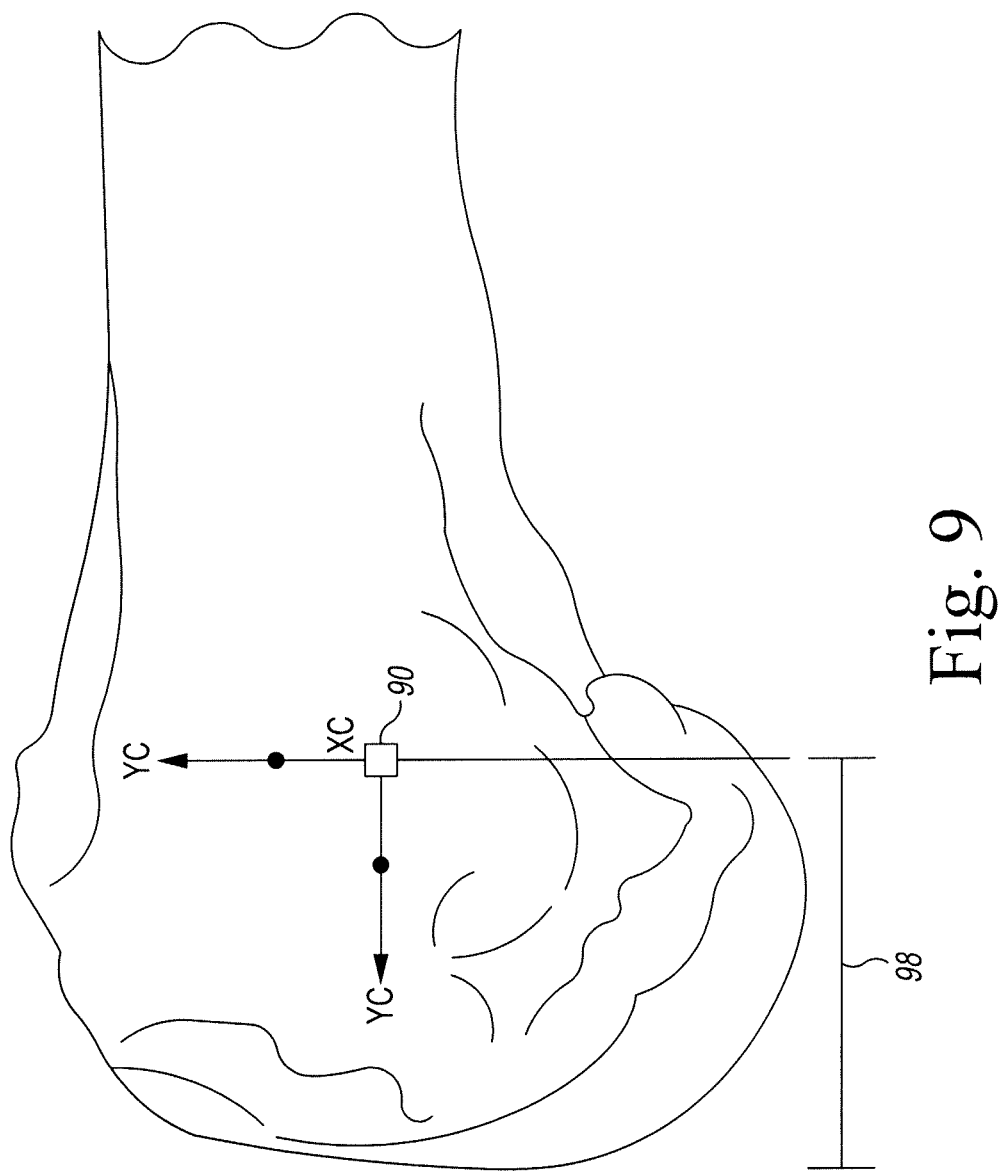

Conversely, in embodiments wherein the relevant patient's bone is embodied as a femur as illustrated in FIGS. 7-9, the reference point 90 is initially located on the most distal point of the distal end of the femoral model 94. Either condyle of the femoral model 94 may be used in various embodiments. Once the reference point 90 is initially established on the most distal point, the reference point 90 is translated to the approximate center of the distal end of the femoral model 94 as illustrated in FIG. 8 such that the Z-axis defining the reference point 90 is parallel to the mechanical axis of the femoral model 92. The anterior-posterior width 96 of the distal end of the femoral model 94 is also determined. Subsequently, as illustrated in FIG. 9, the reference point is moved or otherwise translated in the proximal or superior direction by a distance 98. In one particular embodiment, the reference point is moved in the distal or superior direction by a distance 98 equal to about half the distance 96. As such, it should be appreciated that one of a number of different techniques may be used to define the location of the reference point based on, for example, the type of bone.

Figure 2:
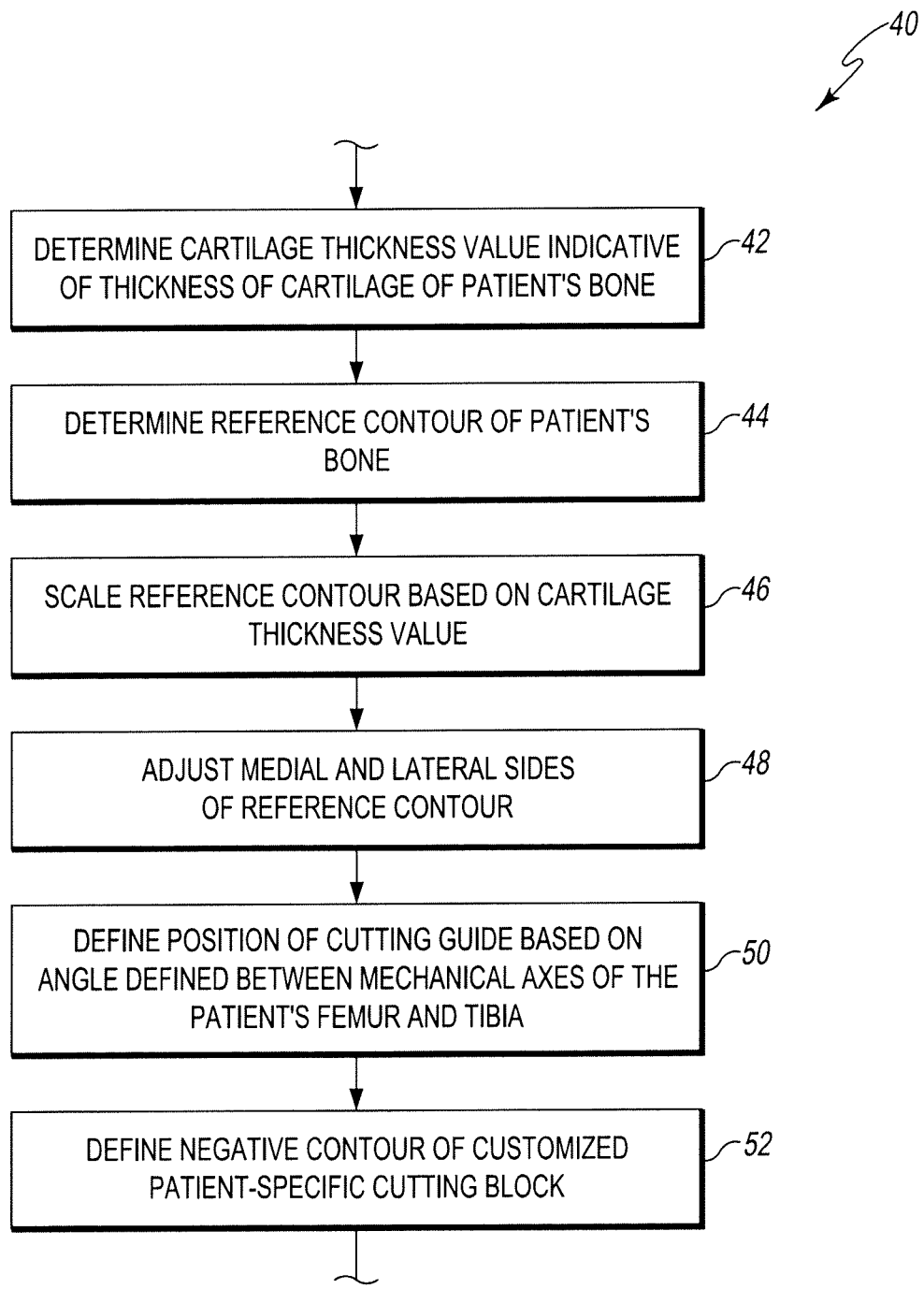
FIG. 2 is a simplified flow diagram of a method for generating a model of a patient-specific orthopaedic instrument.

Referring now back to FIG. 2, once the reference contour has been scaled in step 46, the medial/lateral sides of the reference contour are adjusted in step 48. To do so, in one embodiment, the distance between the reference point and each point lying on, and defining in part, the medial side and lateral side of the reference contour is decreased. For example, in some embodiments, the distance between the reference point and the points on the medial and lateral sides of the scaled reference contour are decreased to the original distance between such points. As such, it should be appreciated that the reference contour is offset or otherwise enlarged with respect to the anterior side of the patient's bone and substantially matches or is otherwise not scaled with respect to the medial and lateral sides of the patient's bone.

The reference contour may also be adjusted in step 48 for areas of the patient's bone having a reduced thickness of cartilage. Such areas of reduced cartilage thickness may be determined based on the existence of bone-on-bone contact as identified in a medical image, simulation, or the like. Additionally, information indicative of such areas may be provided by the orthopaedic surgeon based on his/her expertise. If one or more areas of reduced cartilage thickness are identified, the reference contour corresponding to such areas of the patient's bone is reduced (i.e., scaled back or down).

Additionally, in some embodiments, one or more osteophytes on the patient's bone may be identified; and the reference contour may be compensated for such presence of the osteophytes. By compensating for such osteophytes, the reference contour more closely matches the surface contour of the patient's bone. Further, in some embodiments, a distal end (in embodiments wherein the patient's bone is embodied as a tibia) or a proximal end (in embodiments wherein the patient's bone is embodied as a femur) of the reference contour may be adjusted to increase the conformity of the reference contour to the surface contour of the bone. For example, in embodiments wherein the patient's bone is a femur, the superior end of the scaled reference contour may be reduced or otherwise moved closer to the surface contour of the patient's femur in the region located superiorly to a cartilage demarcation line defined on the patient's femur. Conversely, in embodiments wherein the patient's bone is embodied as a tibia, an inferior end of the scaled reference contour may be reduced or otherwise moved closer to the surface contour of the patient's tibia in the region located inferiorly to a cartilage demarcation line of the patient's tibia. As such, it should be appreciated that the scaled reference contour is initially enlarged to compensate for the thickness of the patient's cartilage on the patient's bone. Portions of the scaled reference contour are then reduced or otherwise moved back to original positions and/or toward the reference point in those areas where cartilage is lacking, reduced, or otherwise not present.

Once the reference contour has been scaled and adjusted in steps 46 and 48, the position of the cutting guide is defined in step 50. In particular, the position of the cutting guide is defined based on an angle defined between a mechanical axis of the patient's femur and a mechanical axis of the patient's tibia. The angle may be determined by establishing a line segment or ray originating from the proximal end of the patient's femur to the distal end of the patient's femur and defining a second line segment or ray extending from the patient's ankle through the proximal end of the patient's tibia. The angle defined by these two line segments/rays is equal to the angle defined between the mechanical axis of the patient's femur and tibia. The position of the bone cutting guide is then determined based on the angle between the mechanical axes of the patient's femur and tibia. It should be appreciated that the position of the cutting guide defines the position and orientation of the cutting plane of the customized patient-specific cutting block. Subsequently, in step 52, a negative contour of the customized patient-specific cutting block is defined based on the scaled and adjusted reference contour and the angle defined between the mechanical axis of the femur and tibia.

Referring back to FIG. 1, after the model of the customized patient-specific orthopaedic surgical instrument has been generated in process step 26, the model is validated in process step 28. The model may be validated by, for example, analyzing the rendered model while coupled to the three-dimensional model of the patient's anatomy to verify the correlation of cutting guides and planes, drilling guides and planned drill points, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

After the model has been validated in process step 28, the customized patient-specific orthopaedic surgical instrument is fabricated in process step 30. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. In fabricating the instrument, customized patient-specific indicia may be applied to the instrument. For example, as noted above, the size of the bone chips produced by proper use of the instrument may be preoperatively determined to facilitate the surgeon's conformance to the surgical plan. Indicia indicative of the size of the bone chips may be applied (e.g., etched, painted, engraved, etcetera) to the outer surface of the instrument in an area near the cutting slot used to create the bone chip. Such indicia makes it easy for the surgeon to quickly ascertain the preoperatively determined size of the bone chip without having to refer to a document or display monitor.

The fabricated customized patient-specific orthopaedic instrument is subsequently shipped or otherwise provided to the orthopaedic surgeon. The surgeon performs the orthopaedic surgical procedure in process step 32 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Figure 10:
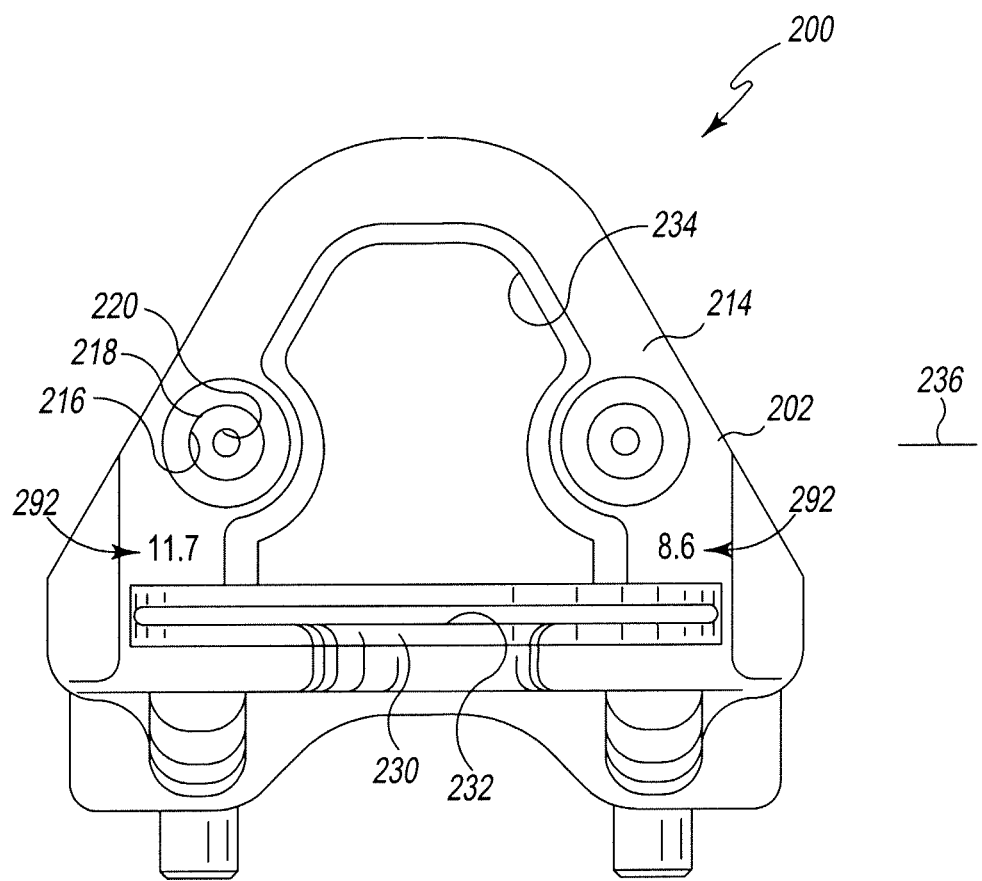
FIG. 10 is an anterior elevation an embodiment of a customized patient-specific orthopaedic surgical instrument.
Figure 11:
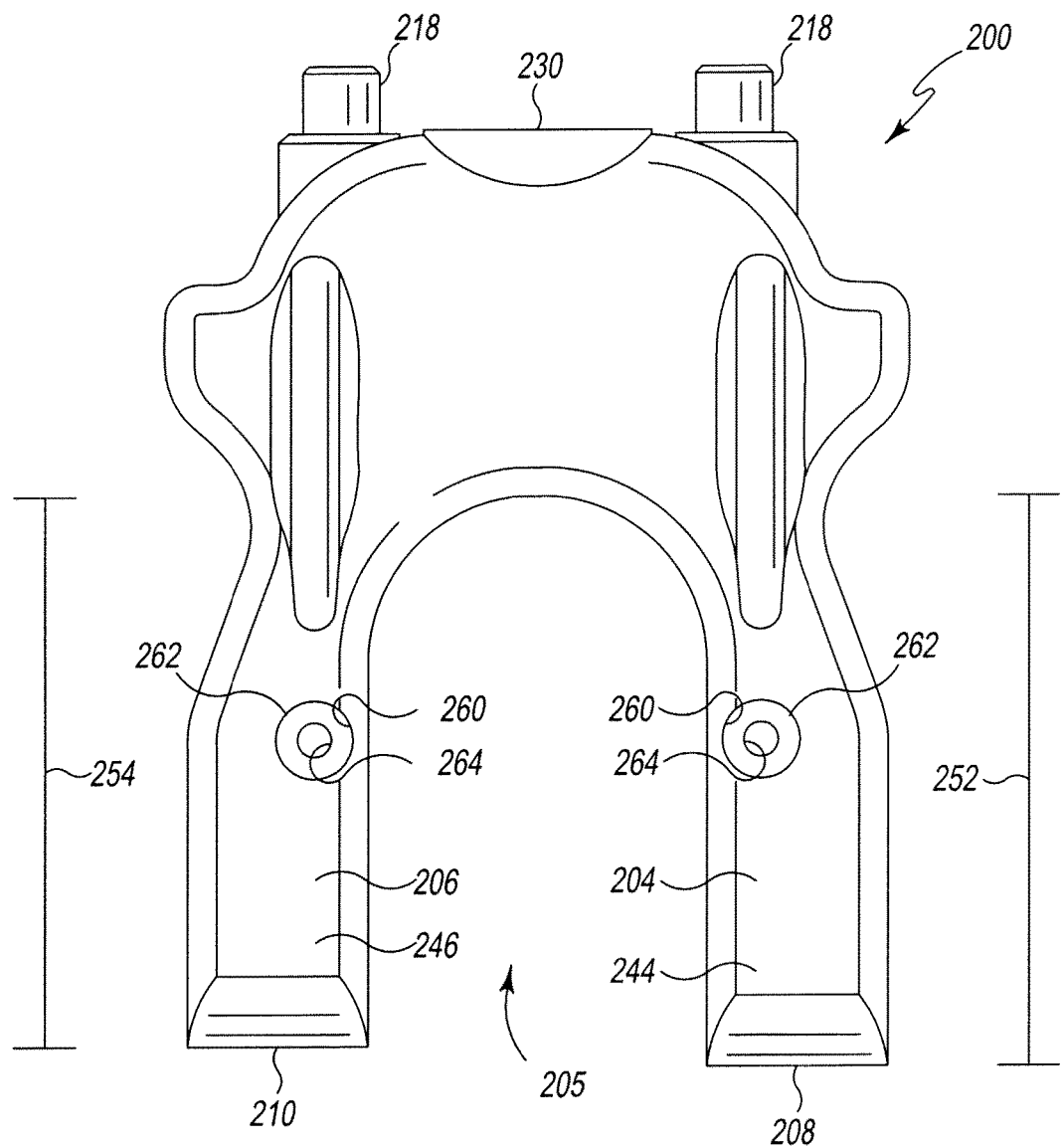
FIG. 11 is a top plan view of the customized patient-specific orthopaedic surgical instrument of FIG. 10.
Figure 12:
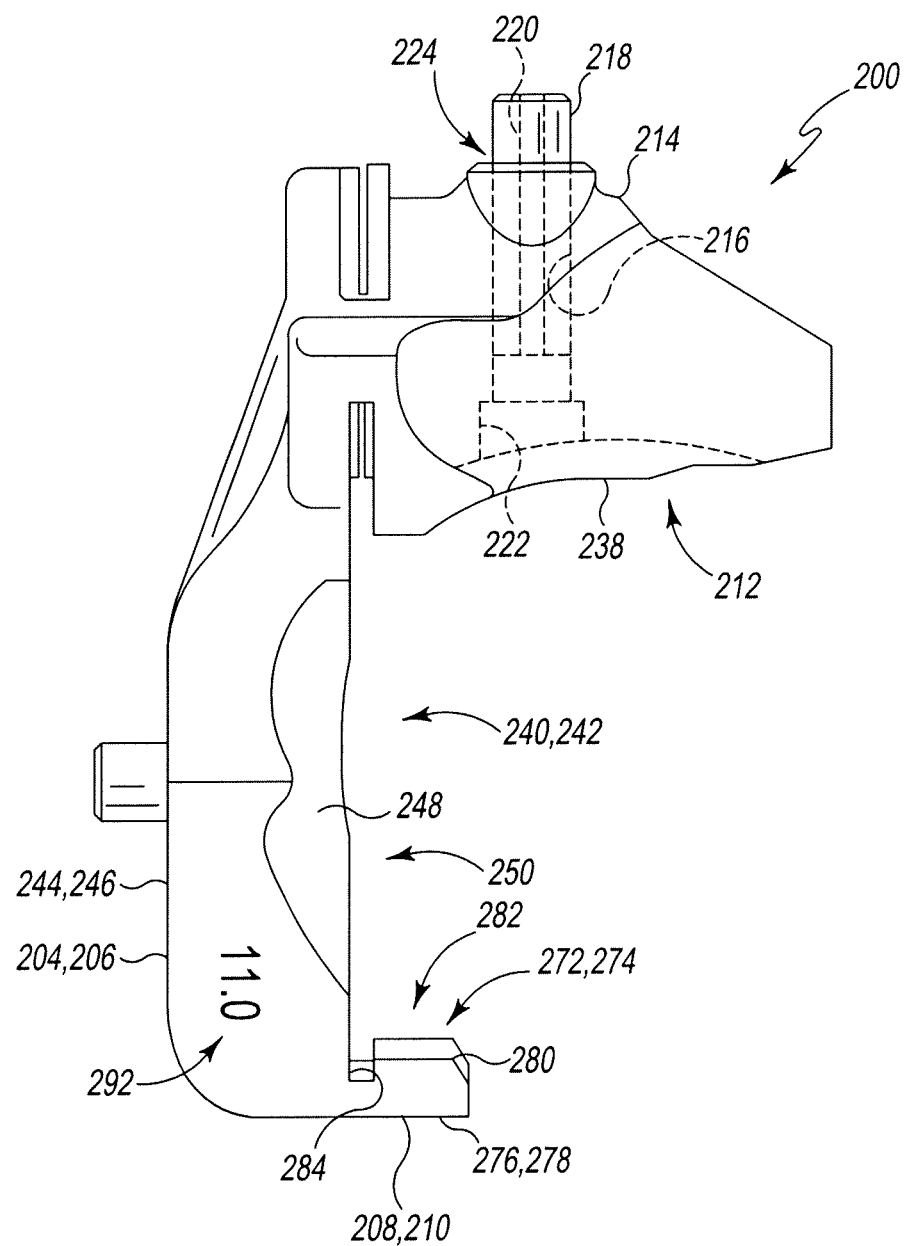
FIG. 12 is side elevation view of the customized patient-specific orthopaedic surgical instrument of FIG. 10.

Referring now to FIGS. 10-12, in one embodiment, the customized patient-specific orthopaedic surgical instrument may be embodied as a femoral cutting block 200. The cutting block 200 is configured to be coupled to a femur of a patient. The cutting block 200 includes a body 202 configured to be coupled to the anterior side of the patient's femur and two arms or tabs 204, 206, which extend away from the body 202 in a posteriorly direction. The tabs 204, 206 are configured to wrap around a distal end of the femur as discussed in more detail below. Each of the tabs 204, 206 includes an inwardly-curving or otherwise superiorly extending lip 208, 210, respectively, which references the posterior condyles of the femur. The cutting block 200 may be formed from any suitable material. For example, the cutting block 200 may be formed from a material such as a plastic or resin material. In one particular embodiment, the cutting block 200 is formed from Vero resin using a rapid prototype fabrication process. However, the cutting block 200 may be formed from other materials in other embodiments. For example, in another particular embodiment, the cutting block 200 is formed from a polyimide thermoplastic resin, such as a Ultem resin, which is commercially available from Saudi Basic Industries Corporation Innovative Plastics of Riyhadh, Saudi Arabia.

The body 202 includes a bone-contacting or bone-facing surface 212 and an outer surface 214 opposite the bone-facing surface 212. The outer surface 214 includes a number of guide holes or passageways 216 defined therethrough. A guide pin bushing 218 is received in each guide hole 216. The guide pin bushings 218 include an internal passageway 220 sized to receive a respective guide pin to secure the block 200 to the patient's femur. As shown in FIG. 12, the guide passageways 216 extends from the outer surface 214 to the bone-facing surface 212 and is counterbored on the bone-facing surface 212. That is, the passageway 216 has an opening 222 on the bone-facing surface 212 having a diameter greater than the diameter of an opening 224 on the outer surface 214

The cutting block 200 includes a cutting guide 230 secured to the body 202. In one particular embodiment, the cutting guide 230 is overmolded to the body 202. The cutting guide 230 includes a cutting guide slot 232. The cutting guide 230 may be formed from the same material as the body 202 or from a different material. In one particular embodiment, the cutting guide 230 is formed from a metallic material such as stainless steel. The body 202 also includes a window or opening 234 defined therethough. The opening 234 allows a surgeon to visualize the positioning of the block 200 on the patient's femur by viewing portions of the femur through the opening 234. Additionally, the opening 234 may reduce the amount of air pockets or other perfections created during the fabrication of the block 200. In the illustrative embodiment, the opening 234 extends from the cutting guide 200 to a point more superior than the superior-most point 236 of the guide pin bushings 218. However, in other embodiments, the cutting block 200 may include windows or openings formed in the body 202 having other shapes and sizes.

The bone-facing surface 212 of the body 202 includes a negative contour 238 configured to receive a portion of the anterior side of the patient's femur having a corresponding contour. As discussed above, the customized patient-specific negative contour 238 of the bone-contacting surface 212 allows the positioning of the cutting block 200 on the patient's femur in a unique pre-determined location and orientation.

The tabs 204, 206 include a bone-contacting or bone-facing surface 240, 242, respectively, and an outer surface 244, 246, respectively, opposite the bone-facing surface 240, 242. The bone-facing surface 240 of the tab 204 includes a negative contour 248 configured to receive a portion of the distal side of the patient's femur having a respective corresponding contour. Similarly, the bone-facing surface 242 of the tab 206 includes a negative contour 250 configured to receive a portion of the distal side of the patient's femur having a respective corresponding contour.

As discussed above, the arms or tabs 204, 206 extend posteriorly from the body 200 to define a U-shaped opening 205 therebetween. The tabs 204, 206 may extend from the body 202 the same distance or a different distance. For example, as shown in FIG. 11, the tab 204 extends from the body 202 a distance 252 and the tab 206 extends from the body 202 a distance 254, which is less than the distance 252. Each of the tabs 204, 206 includes a respective guide hole or passageway 260 defined therethrough. A guide pin bushing 262 is received in each guide hole 260. The guide pin bushings 262 include an internal passageway 264 sized to receive a respective guide pin to further secure the block 200 to the patient's femur. Similar to the guide passageways 216, the guide passageways 260 may be counterbored on the bone-facing surface 240, 242 of the tabs 204, 206.

The lips 208, 210 of the tabs 204, 206 also include a bone-contacting or bone-facing surface 272, 274, respectively, and an outer surface 276, 278, respectively, opposite the bone-facing surface 272, 274. The bone-facing surface 272 of the lip 208 includes a negative contour 280 configured to receive a portion of the posterior side of the patient's femur having a respective corresponding contour. Similarly, the bone-facing surface 274 of the lip 210 includes a negative contour 282 configured to receive a portion of the posterior side of the patient's femur having a respective corresponding contour. Each the lips 208, 210 include a lateral slot 284 that forms a saw relief slot and is configured to provide an amount of clearance for the bone saw blade used to remove a portion of the patient's bone. That is, during the performance of the orthopaedic surgical procedure, a distal end of the bone saw blade may be received in the slot 284.

In addition, in some embodiments, the negative contours 238, 248, 250, 280, 282 of the bone-contacting surfaces 212, 240, 242, 272, 274 of the cutting block 200 may or may not match the remaining corresponding contour surface of the patient's bone. That is, as discussed above, the negative contours 238, 248, 250, 280, 282 may be scaled or otherwise resized (e.g., enlarged) to compensate for the patient's cartilage or lack thereof.

Figure 16:
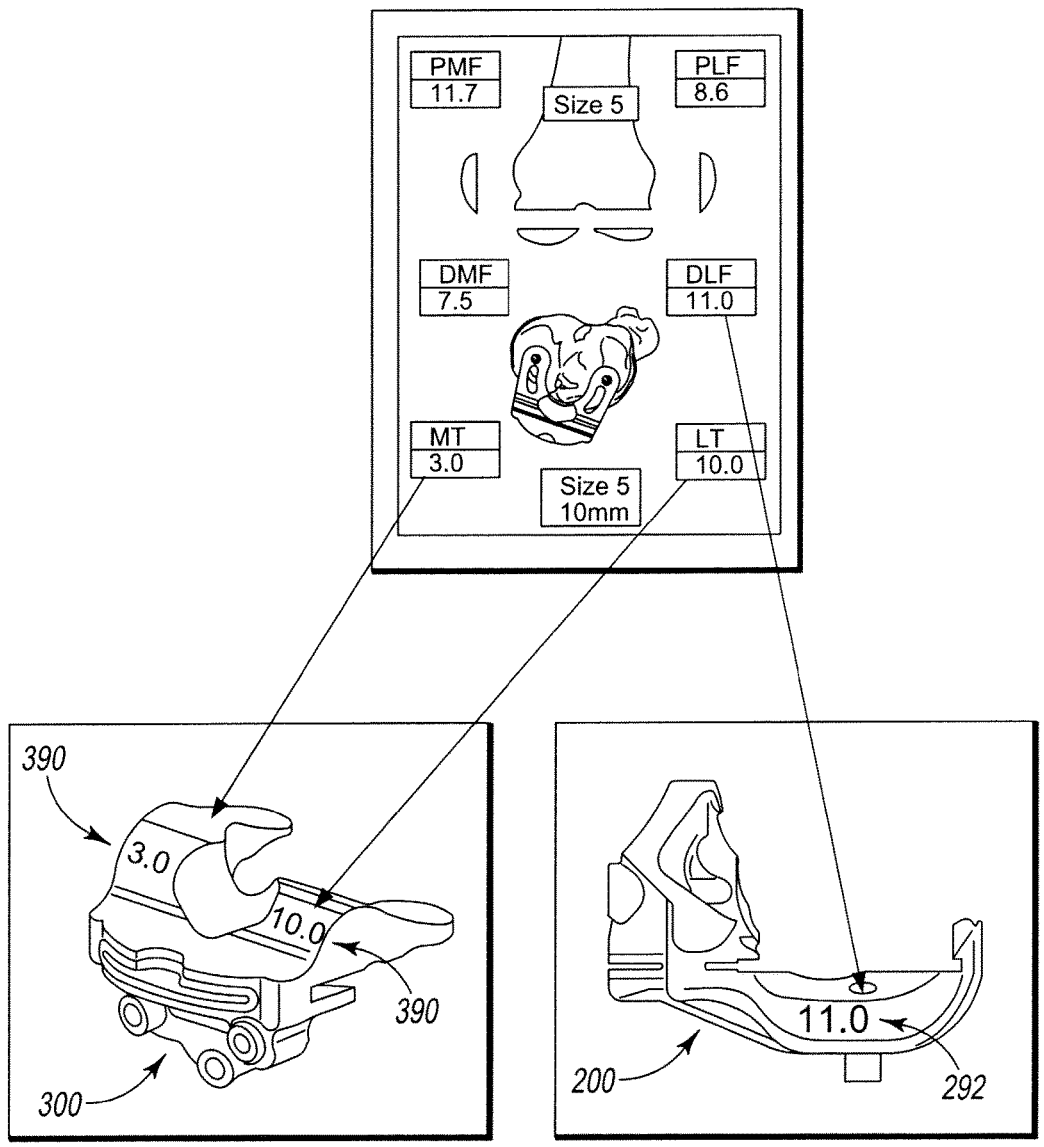
FIG. 16 is a diagrammatic view of showing a visual representation of a surgical design plan and a pair of customized patient-specific orthopaedic surgical instruments based thereon.

As shown in FIG. 16, the femoral cutting block 200 is fabricated based on a surgical design plan that includes, amongst many other things, a determination of the size of the bone chips that will be created when a surgeon resects the patient's femur with the cutting block 200. For example, the design plan used to fabricate the femoral cutting block 200 includes a preoperatively determined size of a distal medial bone chip produced as a result of a surgical resection of the distal medial portion of the patient's distal femur (DMF) with the cutting block 200. It also includes the planned size of a distal lateral bone chip produced as a result of a surgical resection of the distal lateral portion of the patient's distal femur (DLF) with the cutting block 200. The surgical design plan used to fabricate the customized patient-specific femoral cutting block 200 also includes the size of a posterior medial bone chip produced as a result of a surgical resection of the posterior medial portion of the patient's distal femur (PMF) by use of the cutting block 200, and a posterior lateral bone chip produced as a result of a surgical resection of the posterior lateral portion of the patient's distal femur (PLF).

Indicia indicative of the size of each preoperatively planned size of the bone chip is applied to an outer surface of the cutting block. For example, indicia 292 indicative of the preoperatively planned size of a distal medial bone chip produced as a result of a surgical resection of the distal medial portion of the patient's distal femur (DMF) with the cutting block 200 is applied to one of the outer medial surfaces of the body 202 of the cutting block 200. Indicia 292 indicative of the preoperatively planned size of a distal medial bone chip produced as a result of a surgical resection of the distal lateral portion of the patient's distal femur (DLF) with the cutting block 200 is applied to one of the outer lateral surfaces of the body 202 of the cutting block 200. Indicia 292 indicative of the preoperatively planned size of a posterior medial bone chip produced as a result of a surgical resection of the posterior medial portion of the patient's distal femur (PMF) with the cutting block 200 is applied to one of the outer medial or anterior surfaces of the body 202 of the cutting block 200. Indicia 292 indicative of the preoperatively planned size of a posterior lateral bone chip produced as a result of a surgical resection of the posterior lateral portion of the patient's distal femur (PLF) with the cutting block 200 is applied to one of the outer medial or anterior surfaces of the body 202 of the cutting block 200. It should be appreciated that the indicia may be applied to the body 202 of the cutting block 200 in a number of different manners. For example, the indicia 292 may be etched, painted, engraved, etcetera onto the body 202 of the cutting block 200.

In use, the femoral cutting block 200 is coupled to the distal end of the patient's femur. Again, because the bone-contacting surfaces 212, 240, 242, 272, 274 of the cutting block 200 include the negative contours 238, 248, 250, 280, 282, the block 200 may be coupled to the patient's femur in a pre-planned, unique position. When so coupled, the tabs 204, 206 wrap around the distal end of the patient's femur and the lips 208, 210 of the tabs 204, 206 wrap around the posterior side of the patient's femur. Additionally, when the block 200 is coupled to the patient's femur, a portion of the anterior side of the femur is received in the negative contour 238 of the body 202, a portion of the distal side of the patient's femur is received in the negative contours 248, 250 of the tabs 204, 206, and a portion of the posterior side of the femur is received in the negative contours 280, 282 of the lips 208, 210. As such, the anterior, distal, and posterior surfaces of the patient femur are referenced by the femoral cutting block 200.

Once secured to the distal end of the patient's femur, the cutting block 200 is used to resect the patient's bone along the preoperatively planned cutting planes. In doing so, the surgeon produces a distal medial bone chip as a result of resection of the distal medial portion of the patient's distal femur (DMF), and a distal lateral bone chip as a result of resection of the distal lateral portion of the patient's distal femur (DLF). The surgeon also produces a posterior medial bone chip as a result of a surgical resection of the posterior medial portion of the patient's distal femur (PMF), and a posterior lateral bone chip as a result of resection of the posterior lateral portion of the patient's distal femur (PLF). In lieu of simply disregarding or otherwise disposing the bone chips, they are used to validate the surgeon's performance of the surgery in conformance with the preoperative surgical plan. In particular, since the surgeon is aware of the preoperatively determined size of each of the bone chips that are produced if the bone is resected along the preoperatively planned cutting planes, the surgeon can simply measure the actual bone chips created in the surgery and compare them to the preoperatively planned sizes. For example, if a proper resection of the distal medial portion of the patient's distal femur (DMF) according to the preoperative plan should produce a 7.5 mm distal medial bone chip, the surgeon can measure the actual distal medial bone chip produced in the surgery with, for example, a pair of calipers to determine if the chip is, in fact, 7.5 mm. Confirmation of the size of the bone chip is used, therefore, the confirm a proper cut has been made. The surgeon may confirm all four bone chips made during surgical preparation of the patient's femur. If need be, the femur can then be re-cut to remove more bone.

Figure 13:
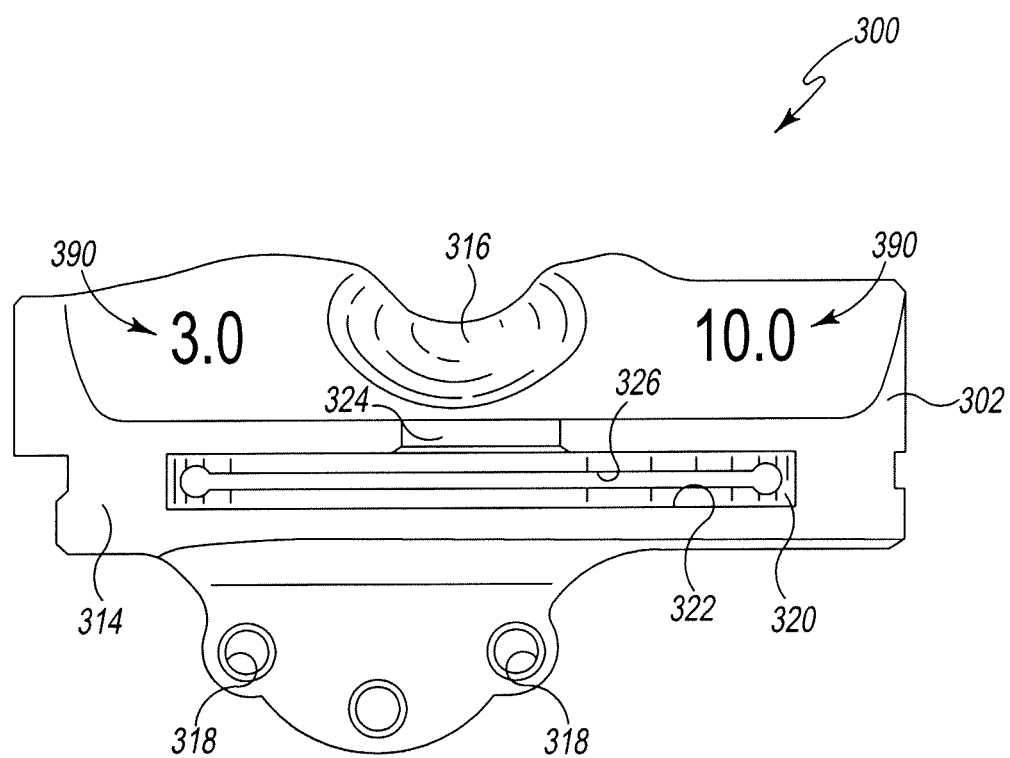
FIG. 13 is an anterior elevation view of another embodiment of a customized patient-specific orthopaedic surgical instrument.
Figure 14:
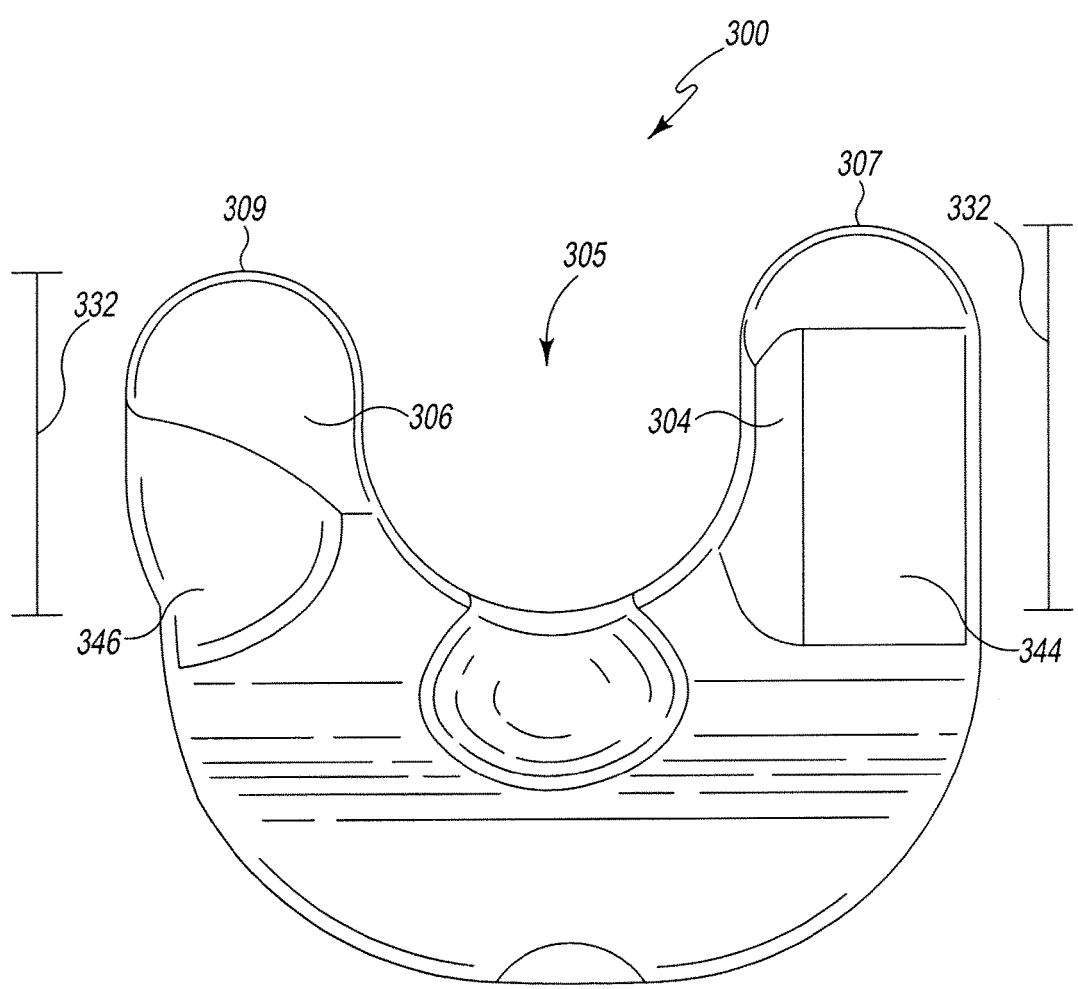
FIG. 14 is a top plan view of the customized patient-specific orthopaedic surgical instrument of FIG. 13.
Figure 15:
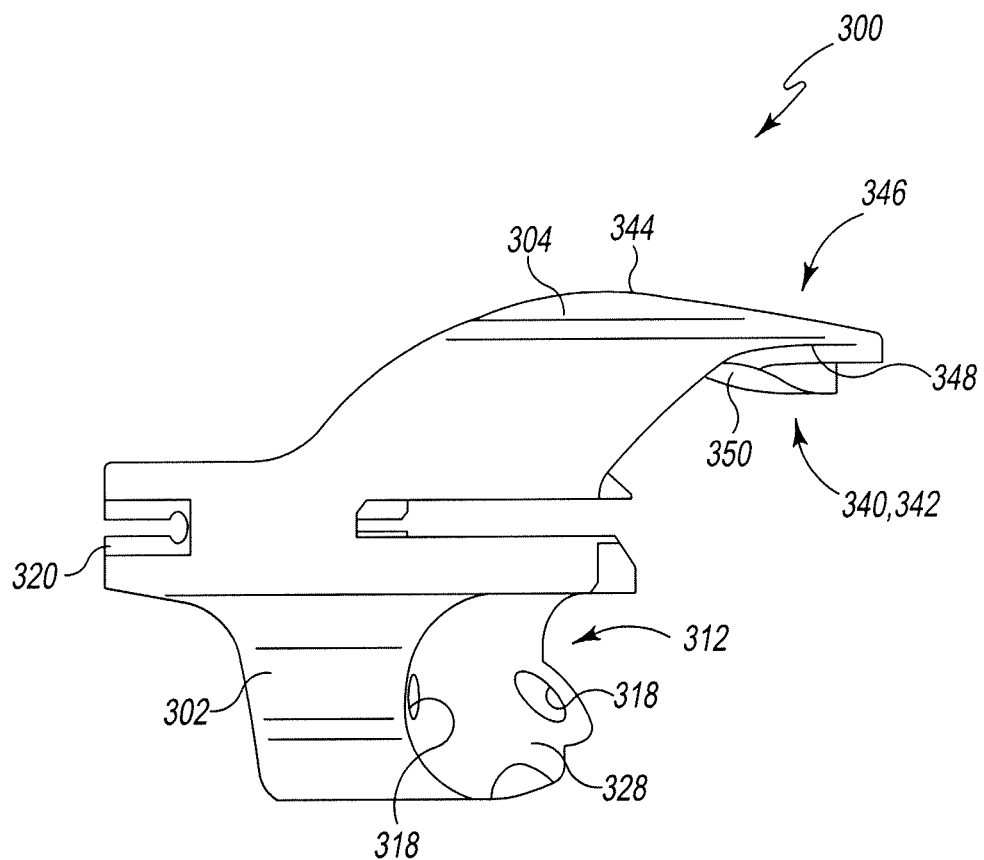
FIG. 15 is side elevation view of the customized patient-specific orthopaedic surgical instrument of FIG. 13.

Referring now to FIGS. 13-15, in another embodiment, the customized patient-specific orthopaedic surgical instrument may be embodied as a tibial cutting block 300. The cutting block 300 is configured to be coupled to a tibia of a patient. The cutting block 300 includes a body 302 configured to be coupled to the anterior side of the patient's tibia and two arms or tabs 304, 306, which extend away from the body 302 in a posteriorly direction. The tabs 304, 306 are configured to wrap over a proximal end of the tibia as discussed in more detail below. The cutting block 300 may be formed from any suitable material. For example, the cutting block 300 may be formed from a material such as a plastic or resin material. In one particular embodiment, the cutting block 300 is formed from Vero resin using a rapid prototype fabrication process. However, the cutting block 300 may be formed from other materials in other embodiments. For example, in another particular embodiment, the cutting block 300 is formed from a polyimide thermoplastic resin, such as a Ultem resin, which is commercially available from Saudi Basic Industries Corporation Innovative Plastics of Riyhadh, Saudi Arabia.

The body 302 includes a bone-contacting or bone-facing surface 312 and an outer surface 314 opposite the bone-facing surface 312. The outer surface 314 includes a depression or recessed area 316, which provides an indication to a surgeon where to apply pressure to the body 302 when coupling the cutting block 300 to the patient's tibia. Additionally, a number of guide pin holes or passageways 318 are defined through the body 302 and have a diameter sized to receive respective guide pins to secure the block 300 to the patient's tibia. In some embodiments, one or more of the guide pin holes 318 may be oblique or otherwise angled with respect to the remaining guide pin holes 318 to further secure the block 300 to the patient's bone.

The body 302 includes a modular cutting guide 320. That is, the body 302 includes a cutting guide receiver slot 322 in which the cutting guide 320 is received. A latch 324 or other locking device secures the cutting guide 320 in place in the cutting guide receiver slot 322. As such, one of a number of different cutting guides 320 having a cutting guide slot 326 defined in various offset positions may be coupled to the body 302 to allow a surgeon to selectively determine the amount of bone of the patient's bone is removed during the bone cutting procedure. For example, a cutting guide 320 having a cutting guide slot 326 offset by +2 millimeters, with respect to a neutral reference cutting guide 320, may be used if the surgeon desires to remove a greater amount of the patient's bone. The cutting guide 320 may be formed from the same material as the body 302 or from a different material. In one particular embodiment, the cutting guide 320 is formed form a metallic material such as stainless steel. It should be appreciated that the cutting block 300 may be embodied without a modular cutting guide 320. That is, the cutting block 300 may be embodied with a fixed cutting guide 320 that is overmolded into the polymer body 302

The bone-facing surface 312 of the body 302 includes a negative contour 328 configured to receive a portion of the anterior side of the patient's tibia having a corresponding contour. As discussed above, the customized patient-specific negative contour 328 of the bone-contacting surface 312 allows the positioning of the cutting block 300 on the patient's tibia in a unique pre-determined location and orientation.

As discussed above, the arms or tabs 304, 306 extend posteriorly from the body 302 to define a U-shaped opening 305 therebetween. The tabs 304, 306 may extend from the body 302 the same distance or a different distance. For example, as shown in FIG. 14, the tab 304 extends from the body 302 a distance 330 and the tab 306 extends from the body 302 a distance 332, which is greater than the distance 330. The tabs 304, 306 taper in the anterior-posterior direction. That is, the thickness of the tabs 304, 306 at an anterior end of the tabs 304, 306 is greater than the thickness of the tabs 304, 306 at a respective posterior end 307, 309. The tapering of the tabs 304, 306 allow the tabs 304, 306 to be inserted within the joint gap defined between the patient's femur and tibia.

The tabs 304, 306 include a bone-contacting or bone-facing surface 340, 342, respectively, and an outer surface 344, 346, respectively, opposite the bone-facing surface 340, 342. The bone-facing surface 340 of the tab 304 includes a negative contour 348 configured to receive a portion of the patient's proximal tibia having a respective corresponding contour. Similarly, the bone-facing surface 342 of the tab 306 includes a negative contour 350 configured to receive a portion of the patient's proximal tibia having a respective corresponding contour.

In addition, in some embodiments, the negative contours 328, 348, 350 of the bone-contacting surfaces 312, 340, 342 of the cutting block 300 may or may not match the remaining corresponding contour surface of the patient's bone. That is, as discussed above, the negative contours 328, 348, 350 may be scaled or otherwise resized (e.g., enlarged) to compensate for the patient's cartilage or lack thereof.

As shown in FIG. 16, the tibial cutting block 300 is fabricated based on a surgical design plan that includes, amongst many other things, a determination of the size of the bone chips that will be created when a surgeon resects the patient's tibia with the cutting block 300. For example, the design plan used to fabricate the tibial cutting block 300 includes the preoperatively determined size of the bone chip (or chips) produced as a result of a surgical resection of the proximal medial portion (MT) and the proximal lateral portion (LT) of the patient's proximal tibia with the cutting block 300. Indicia indicative of the size of such preoperatively planned bone chip(s) is applied to an outer surface of the cutting block 300. For example, indicia 390 indicative of the preoperatively planned size of a bone chip produced as a result of a surgical resection of the proximal medial portion (MT) and the proximal lateral portion (LT) of the patient's proximal tibia with the cutting block 300 is applied to one of the outer anterior surfaces of the body 302 of the cutting block 300. It should be appreciated that the indicia may be applied to the body 302 of the cutting block 300 in a number of different manners. For example, the indicia 390 may be etched, painted, engraved, etcetera onto the body 302 of the cutting block 300.

In use, the tibial cutting block 300 is coupled to the proximal end of the patient's tibia. Again, because the bone-contacting surfaces 312, 340, 342 of the cutting block 300 include the negative contours 328, 348, 350, the block 300 may be coupled to the patient's tibia in a pre-planned, unique position. When so coupled, the tabs 304, 306 wrap around the proximal end of the patient's tibia. Additionally, when the block 300 is coupled to the patient's tibia, a portion of the anterior side of the tibia is received in the negative contour 328 of the body 302 and a portion of the proximal side of the patient's tibia is received in the negative contours 348, 350 of the tabs 304, 306. As such, the anterior and proximal surfaces of the patient tibia are referenced by the tibial cutting block 300.

Once secured to the distal end of the patient's tibia, the cutting block 300 is used to resect the patient's bone along the preoperatively planned cutting planes. In doing so, the surgeon produces a bone chip (or chips) as a result of a surgical resection of the proximal medial portion (MT) and the proximal lateral portion (LT) of the patient's proximal tibia. In lieu of simply disregarding or otherwise disposing the bone chip(s), it is used to validate the surgeon's performance of the surgery in conformance with the preoperative surgical plan. In particular, since the surgeon is aware of the preoperatively determined size of the bone chip(s) produced if the tibia is resected along the preoperatively planned cutting plane(s), the surgeon can simply measure the actual bone chip(s) created in the surgery and compare it to the preoperatively planned size. For example, if a proper resection of the of the proximal medial portion (MT) and the proximal lateral portion (LT) of the patient's proximal tibia should produce a bone chip that is 3.0 mm thick on the proximal medial side (MT) and 10.0 mm thick on the proximal lateral side (LT), the surgeon can measure the actual bone chip produced in the surgery with, for example, a pair of calipers to determine if the chip is, in fact, 3.0 mm thick on the proximal medial side (MT) and 10.0 mm thick on the proximal lateral side (LT). Confirmation of the size of the bone chip is used, therefore, the confirm a proper cut has been made. If need be, the tibia can then be re-cut to remove more bone.

It should be appreciated that certain aspects of the methods described herein may be utilized without the use of customized patient-specific instruments. For example, a surgical design plan can be preoperatively designed in the manner described herein, including a determination of the sizes of the various bone chips that are to be created if a resection of the patient's bone is performed according to the plan. However, the plan may contemplate that the actual resection will be performed with standard instruments (i.e., instruments that are not customized for a particular patient). In such a case, the surgical design plan alone is the output from the preoperative design process. The plan may be transmitted to the surgeon via a printed document or electronic file, and, like the other plans described herein, may include electronic and/or visual representations of the plan's various features.

Like the process described above utilizing customized patient-specific instruments, the surgeon may use information from the preoperatively designed surgical plan even though customized instruments are not being used. For example, the surgeon can utilize the preoperatively planned cutting planes to perform the cuts on the patient's bone. Moreover, the surgeon can save and thereafter measure the resultant bone chips to confirm the surgeon's conformance with the plan.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

What is claimed is:

1. A method for a vendor to create a customized patient-specific orthopaedic instrument for a patient of a healthcare facility that is external to the vendor, comprising:
   receiving, from the healthcare facility external to the vendor, an instrument request that includes data relevant to a bone of the patient,
   creating, in response to receiving the instrument request, a surgical design plan that has been customized for the patient per data of the instrument request, the surgical design plan comprising a preoperatively planned size of at least one bone chip produced as a result of a surgical resection of the bone of the patient consistent with the surgical design plan,
   sending the surgical design plan to the healthcare facility, and
   operating a manufacturing machine located at the vendor to fabricate the customized patient-specific orthopaedic instrument per data of the surgical design plan, and sending the fabricated customized patient-specific orthopaedic instrument to the healthcare facility.

2. The method of claim 1, wherein sending the surgical design plan comprises transmitting the surgical design plan to the healthcare facility via a network.

3. The method of claim 1, wherein sending the design plan comprises mailing the surgical design plan to the healthcare facility.

4. The method of claim 1, wherein:
the data relevant to the bone of the patient comprises one or more medical images of the bone of the patient, and
creating the surgical design plan comprises creating the surgical design plan based upon the one or more medical images of the bone of the patient.

5. The method of claim 1, wherein:
the data relevant to the bone of the patient comprises one or more medical images of the femur of the patient, and
creating the surgical design plan comprises creating a surgical design plan that comprises a preoperatively planned size of (i) a distal medial bone chip produced as a result of a surgical resection of the distal medial portion of the patient's distal femur consistent with the surgical design plan, and (ii) a distal lateral bone chip produced as a result of a surgical resection of the distal lateral portion of the patient's distal femur consistent with the surgical design plan.

6. The method of claim 5, wherein creating the surgical design plan further comprises creating a surgical design plan that comprises a preoperatively planned size of (i) a posterior medial bone chip produced as a result of a surgical resection of the posterior medial portion of the patient's distal femur consistent with the surgical design plan, and (ii) a posterior lateral bone chip produced as a result of a surgical resection of the posterior lateral portion of the patient's distal femur consistent with the surgical design plan.

7. The method of claim 1, wherein:
the data relevant to the bone of the patient comprises one or more medical images of the tibia of the patient, and
creating the surgical design plan comprises creating a surgical design plan that comprises a preoperatively planned size of a bone chip produced as a result of a surgical resection of the proximal medial portion and the proximal lateral portion of the patient's proximal tibia consistent with the surgical design plan.

8. The method of claim 1, wherein creating the surgical design plan comprises creating a surgical design plan that comprises a visual indication of the bone chip produced as a result of the surgical resection of the bone of the patient consistent with the surgical design plan.

9. A method of performing an orthopaedic surgical procedure on a bone of a patient at a healthcare facility, comprising:
making a cut in the bone of the patient at a location indicated in a surgical design plan obtained from a vendor that is external to the healthcare facility that has been customized for the patient per data relevant to a bone of the patient, the surgical design plan comprising a preoperatively planned size of a bone chip produced as a result of the cut,
measuring the actual size of the bone chip produced as a result of the cut, and
comparing the measured actual size of the bone chip to the preoperatively planned size of the bone chip of the surgical design plan.

10. The method of claim 9, wherein making the cut comprises making the cut with a customized patient-specific orthopaedic cutting block fabricated per data of the surgical design plan.

11. The method of claim 9, wherein making the cut on the bone of the patient comprises making a cut in the bone of the patient at a location indicated in a surgical design plan obtained from a vendor that is external to the healthcare facility that has been customized for the patient per one or more medical images of the bone of the patient.

12. The method of claim 9, wherein:
the surgical design plan comprises a preoperatively planned size of (i) a distal medial bone chip produced as a result of a surgical resection of the distal medial portion of the patient's distal femur consistent with the surgical design plan, and (ii) a distal lateral bone chip produced as a result of a surgical resection of the distal lateral portion of the patient's distal femur consistent with the surgical design plan,
making the cut comprises (i) resecting the distal medial portion of the patient's distal femur to produce a distal medial bone chip, and (ii) resecting the distal lateral portion of the patient's distal femur to produce a distal lateral bone chip,
measuring the actual size of the bone chip comprises measuring the actual size of the distal medial bone chip and the distal lateral bone chip, and
comparing the measured actual size of the bone chip comprises (i) comparing the measured actual size of the distal medial bone chip to the preoperatively planned size of the distal medial bone chip of the surgical design plan, and (ii) comparing the measured actual size of the distal lateral bone chip to the preoperatively planned size of the distal lateral bone chip of the surgical design plan.

13. The method of claim 12, wherein:
the surgical design plan further comprises a predetermined size of (i) a posterior medial bone chip produced as a result of a surgical resection of the posterior medial portion of the patient's distal femur consistent with the surgical design plan, and (ii) a posterior lateral bone chip produced as a result of a surgical resection of the posterior lateral portion of the patient's distal femur consistent with the surgical design plan,
making the cut further comprises (i) resecting the posterior medial portion of the patient's distal femur to produce a posterior medial bone chip, and (ii) resecting the posterior lateral portion of the patient's distal femur to produce a posterior lateral bone chip,
measuring the actual size of the bone chip further comprises measuring the actual size of the posterior medial bone chip and the posterior lateral bone chip, and
comparing the measured actual size of the bone chip further comprises (i) comparing the measured actual size of the posterior medial bone chip to the preoperatively planned size of the posterior medial bone chip of the surgical design plan, and (ii) comparing the measured actual size of the posterior lateral bone chip to the preoperatively planned size of the posterior lateral bone chip of the surgical design plan.

14. The method of claim 9, wherein:
the surgical design plan comprises a preoperatively planned size of a bone chip produced as a result of a surgical resection of the proximal medial portion and the proximal lateral portion of the patient's proximal tibia consistent with the surgical design plan, and making the cut comprises resecting the proximal medial portion and the proximal lateral portion of the patient's proximal tibia to produce a bone chip.

15. The method of claim 9, wherein measuring the actual size of the bone chip comprises measuring the actual size of the bone chip with calipers.

16. The method of claim 9, wherein measuring the actual size of the bone chip comprises measuring the actual size of the bone chip with calipers.

17. A method of performing an orthopaedic surgical procedure on a bone of a patient, comprising:
- preoperatively planning a size of a bone chip to be produced by resecting the bone of the patient at a predetermined location,
- making a cut in the bone of the patient at the predetermined location thereby producing a bone chip,
- measuring the actual size of the bone chip produced as a result of the cut,
- comparing the measured actual size of the bone chip to the preoperatively planned size of the bone chip, and
- re-cutting the bone of the patient if the measured actual size of the bone chip is smaller than the preoperatively planned size of the bone chip.

* * * * *